United States Patent
Lee et al.

(10) Patent No.: US 10,094,807 B2
(45) Date of Patent: Oct. 9, 2018

(54) ULTRASOUND IMAGING APPARATUS AND METHOD OF CONTROLLING THE SAME

(71) Applicant: SAMSUNG MEDISON CO., LTD., Gangwon-do (KR)

(72) Inventors: Sang-Mok Lee, Seoul (KR); Nam-Woong Kim, Seoul (KR); Hong-Gyo Lee, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 463 days.

(21) Appl. No.: 14/789,759

(22) Filed: Jul. 1, 2015

(65) Prior Publication Data
US 2016/0238563 A1 Aug. 18, 2016

(30) Foreign Application Priority Data
Feb. 13, 2015 (KR) .................. 10-2015-0021964

(51) Int. Cl.
*A61B 8/00* (2006.01)
*G01N 29/24* (2006.01)
*G01S 7/52* (2006.01)

(52) U.S. Cl.
CPC ........... *G01N 29/24* (2013.01); *A61B 8/4405* (2013.01); *A61B 8/4411* (2013.01); *A61B 8/4444* (2013.01); *A61B 8/4477* (2013.01); *G01S 7/52082* (2013.01); *A61B 8/467* (2013.01)

(58) Field of Classification Search
CPC ....................................... G01N 29/24
USPC ........................................ 73/620
See application file for complete search history.

(56) References Cited

U.S. PATENT DOCUMENTS

| | | | |
|---|---|---|---|
| 2002/0146927 A1 | 10/2002 | Uchibori et al. | |
| 2006/0036177 A1 | 2/2006 | Onodera | |
| 2009/0069690 A1 | 3/2009 | Shin et al. | |
| 2010/0018314 A1 | 1/2010 | Oonuki et al. | |
| 2012/0078109 A1* | 3/2012 | Okuno ............ | A61B 8/56 600/459 |
| 2016/0007958 A1* | 1/2016 | Giral .............. | A61B 8/4477 600/437 |

FOREIGN PATENT DOCUMENTS

| | | |
|---|---|---|
| EP | 0528693 A1 | 2/1993 |
| EP | 2609867 A1 | 7/2013 |
| JP | 2008-148841 A | 7/2008 |
| KR | 10-2005-0065910 A | 11/2006 |
| WO | 2014/128519 A1 | 8/2014 |

OTHER PUBLICATIONS

Extended European Search Report issued in European Application No. 15169411.4 dated Jun. 17, 2016.

* cited by examiner

*Primary Examiner* — Walter L Lindsay, Jr.
*Assistant Examiner* — Philip Marcus T Fadul
(74) *Attorney, Agent, or Firm* — McDermott Will & Emery LLP

(57) ABSTRACT

Disclosed herein is an ultrasound imaging apparatus including a beamformer to transmit or receive an ultrasound signal; a first probe connection unit in which a first probe connector is placed; and a second probe connection unit in which a second probe connector is placed. The second probe connection unit is connected to the beamformer via the first probe connection unit, and the first probe connection unit includes a disconnecting unit to disconnect the first probe connection unit and the second probe connection unit from each other.

22 Claims, 26 Drawing Sheets

ULTRASOUND IMAGING APPARATUS AND METHOD OF CONTROLLING THE SAME

CROSS-REFERENCE TO RELATED APPLICATION

This application claims priority from Korean Patent Application No. 10-2015-0021964, filed on Feb. 13, 2015 in the Korean Intellectual Property Office, the disclosure of which is incorporated herein in its entirety by reference.

BACKGROUND

1. Field

Apparatuses and methods consistent with exemplary embodiments relate to an ultrasound imaging apparatus for generating an ultrasound image, and a method of controlling the same.

2. Description of the Related Art

An ultrasound imaging apparatus provides information regarding a desired region of an object to be tested by transmitting an ultrasound signal from a surface of the object into the object and detecting an ultrasound signal reflected from the object, i.e., an ultrasound echo signal, so as to generate an image of the inner region of the object, such as a tomographic image of a soft tissue or an image of a blood flow.

The ultrasound imaging apparatus has a small size, is cheap, and has non-invasive and non-destructive characteristics, compared to other image diagnosis apparatuses such as an X-ray apparatus, a computerized tomography (CT) scanner, a magnetic resonance image (MRI) apparatus, a nuclear medicine diagnosis apparatus, etc. Thus, the ultrasound imaging apparatus has been used in various medical fields including an obstetric and gynecologic diagnosis, a cardiac diagnosis, an abdominal diagnosis, a urologic diagnosis, etc.

The ultrasound imaging apparatus includes a body configured to accommodate main components of the ultrasound imaging apparatus; and a probe assembly that includes a probe for transmitting an ultrasound signal to an object and receiving an ultrasound echo signal reflected from the object so as to obtain an ultrasound image of the object, and a probe connector connected to the body.

SUMMARY

Therefore, it is an aspect of the present invention to provide an ultrasound imaging apparatus in which an ultrasound signal is transmitted or received through electric connection to a probe connector selected by a user in a body in which a plurality of probe connectors are installed, and non-selected probe assemblies are disconnected, and a method of controlling the same.

Additional aspects of the invention will be set forth in part in the description which follows and, in part, will be obvious from the description, or may be learned by practice of the invention.

In accordance with one aspect of the present invention, an ultrasound imaging apparatus includes a beamformer to transmit or receive an ultrasound signal; a first probe connection unit in which a first probe connector is placed; and a second probe connection unit in which a second probe connector is placed. The second probe connection unit is connected to the beamformer via the first probe connection unit. The first probe connection unit includes a disconnecting unit to disconnect the first probe connection unit and the second probe connection unit from each other.

The ultrasound imaging apparatus may further include a controller to control the first and second probe connection units. The first probe connection unit may include a locking unit to lock the first probe connector into the first probe connection unit and the second probe connection unit may include a locking unit to lock the second probe connector into the second probe connection unit, based on a control signal generated by the controller.

When the first probe connector is locked into the first probe connection unit, the disconnecting unit may disconnect the first probe connection unit and the second probe connection unit from each other.

The first and second probe connectors may be locked into the first and second probe connection units, respectively, through a user's manual manipulation.

The disconnecting unit may include at least one among an analog switch, a field-effect transistor (FET), an integrated circuit, and micro-electromechanical systems (MEMS) to disconnect the first probe connection unit and the second probe connection unit.

The first probe connection unit may further include a socket pin configured to transmit or receive an ultrasound signal when the socket pin comes in contact with an connection pin of the first probe connector. The disconnecting unit may disconnect the first probe connection unit and the second probe connection unit when the connection pin comes in contact with the socket pin.

The socket pin may be formed in a convex shape, and connected to the beamformer and the disconnecting unit. The disconnecting unit may be connected to the socket pin, the beamformer, and the second probe connection unit, and disconnect the first probe connection unit and the second probe connection unit when a physical force is applied to a convex portion of the socket pin.

The socket pin may have a convex portion. One end of the socket pin may be connected to the beamformer. The socket pin may be connected to the disconnecting unit when another end of the socket pin comes in contact with the disconnecting unit. One end of the disconnecting unit may be connected to the second probe connection unit. The disconnecting unit may be connected to the socket pin when the socket pin comes in contact with the disconnecting unit. The other end of the socket pin may be separated from the other end of the disconnecting unit when a physical force is applied to the convex portion of the socket pin The socket pin may have a central protruding portion, a central end of the socket pin may be connected to the beamformer, and both ends of the socket pin may be connected to the second probe connection unit. A plurality of holes may be formed in the both ends of the socket pin, through which the disconnecting unit passes. One end of the disconnecting unit may pass through one of the plurality of holes as the disconnecting unit is moved to the left or the right, and another end of the disconnecting unit may cause the socket pin to be separated from the second probe connection unit.

The ultrasound imaging apparatus may further include a controller to control the disconnecting unit. The disconnecting unit may be moved to the left or the right according to a control signal generated by the controller or through a user's manipulation.

The first probe connection unit may further include a driving device to cause the connection pin of the first probe connector and the socket pin to contact each other.

The driving device may include a motor or an actuator.

The ultrasound imaging apparatus may further include a controller to control the disconnecting unit. The disconnecting unit may change a direction in which the first probe connection unit and the second probe connection unit are to be disconnected from each other, according to a control signal generated by the controller or through a user's manipulation.

The ultrasound imaging apparatus may further include an input device to receive a command to select a first probe or a second probe from a user. When the first probe is selected, the disconnecting unit may disconnect the first probe connection unit and the second probe connection unit from each other.

The ultrasound imaging apparatus may further include an image processor to generate image data based on an ultrasound signal received from the first or second probe selected by the user; and a display device to display an ultrasound image based on the image data.

The ultrasound imaging apparatus may further include a third probe connection unit in which a third probe connector is placed. The third probe connection unit may be connected to the beamformer via the first and second probe connection units. The second probe connection unit may include a disconnecting unit to disconnect the second probe connection unit and the third probe connection unit from each other.

In accordance with another aspect of the present invention, an ultrasound imaging apparatus includes a beamformer to transmit or receive an ultrasound signal; a first probe connection unit in which a first probe connector is placed; a second probe connection unit in which a second probe connector is placed, the second probe connection unit connected to the beamformer via the first probe connection unit; and a disconnecting unit to disconnect the first probe connection unit and the second probe connection unit.

The ultrasound imaging apparatus may further include a controller to control the first and second probe connection units. The first probe connection unit may include a locking unit to lock the first probe connector into the first probe connection unit and the second probe connection unit may include a locking unit to lock the second probe connector into the second probe connection unit, based on a control signal generated by the controller.

The disconnecting unit may include at least one among an analog switch, a field-effect transistor (FET), an integrated circuit, and micro-electromechanical systems (MEMS) to disconnect the first probe connection unit and the second probe connection unit.

The disconnecting unit may cause a transmission line of the first probe connection unit and a transmission line of the second probe connection unit to be separated from each other or to contact each other.

The first and second probe connectors may be locked into the first and second probe connection units, respectively, through a user's manual manipulation.

In accordance with another aspect of the present invention, there is provided a method of controlling an ultrasound imaging apparatus which includes a first probe connection unit in which a first probe connector is placed and a second probe connection unit in which a second probe connector is placed, the method including receiving a command to select a first probe or a second probe from a user; locking the first probe connector including the first probe when the first probe is selected; and disconnecting the second probe connection unit, which is connected to the beamformer via the first probe connection unit, from the first probe connection unit.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
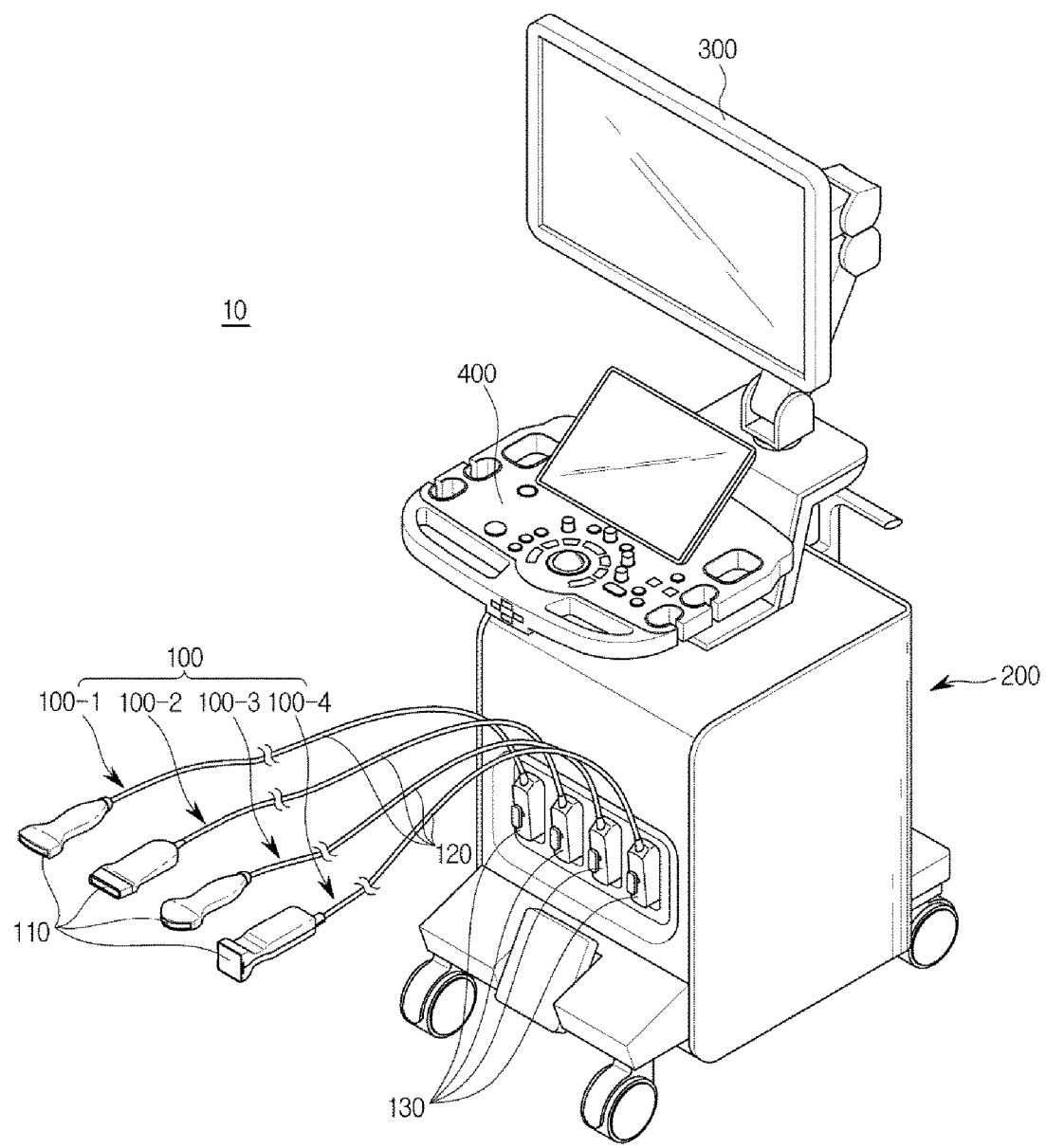
FIG. 1 is a perspective view of the exterior of an ultrasound imaging apparatus in accordance with one embodiment of the present invention.

Reference will now be made in detail to exemplary embodiments with reference to the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description.

Hereinafter, an ultrasound imaging apparatus and a controlling method thereof in accordance with exemplary embodiments of the present invention will be described in detail with reference to the accompanying drawings.

Figure 2:
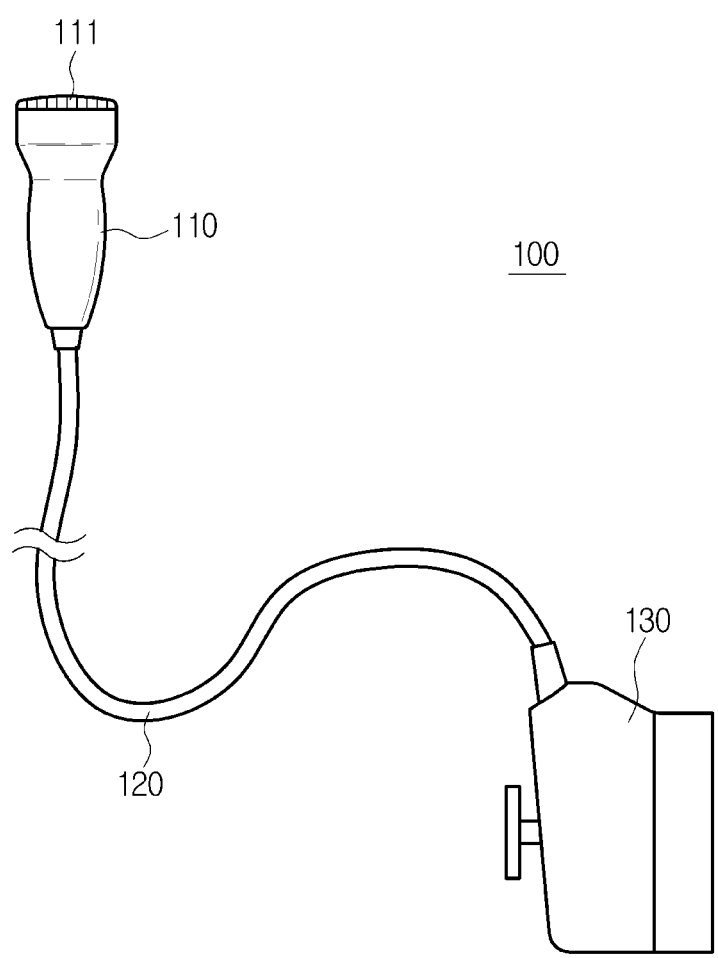
FIG. 2 is a conceptual diagram of the exterior of a probe assembly.
Figure 3A:
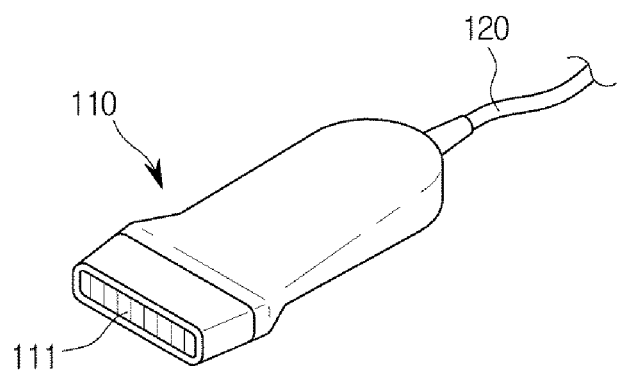
FIGS. 3A to 3C illustrate shapes of various probe assemblies.
Figure 3B:
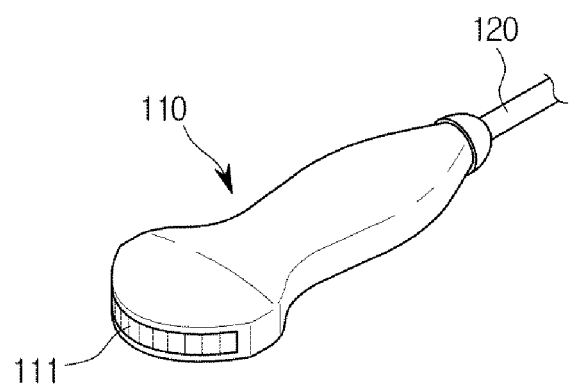
Figure 3C:
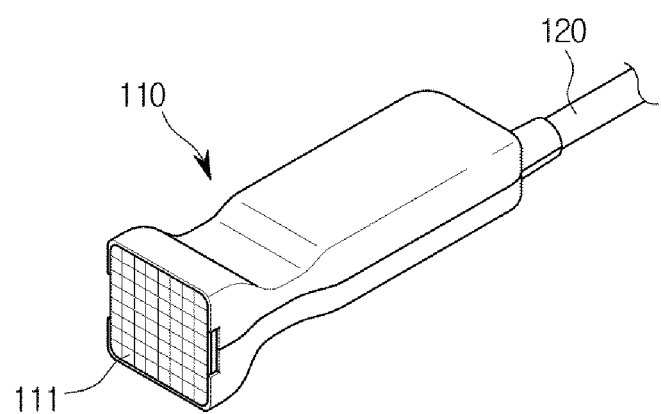
Figure 4:
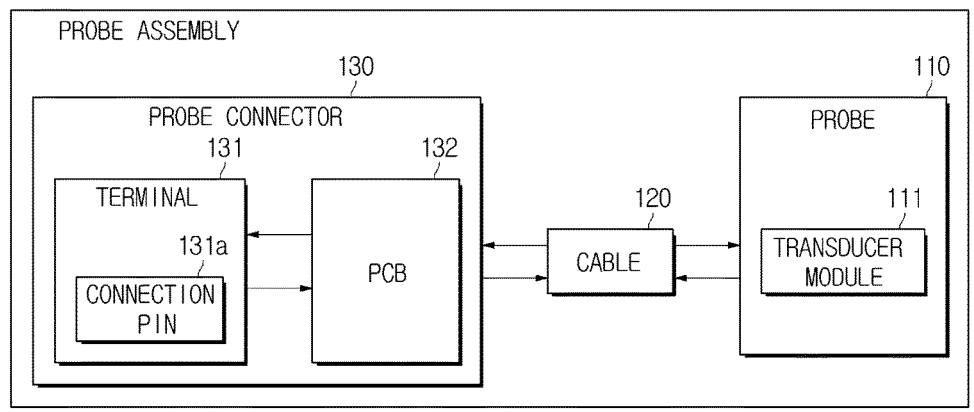
FIG. 4 is a control block diagram of a probe assembly in accordance with one embodiment of the present invention.

FIG. 1 is a perspective view of the exterior of an ultrasound imaging apparatus in accordance with one embodiment of the present invention. FIG. 2 is a conceptual diagram of the exterior of a probe assembly. FIGS. 3A to 3C illustrate shapes of various probe assemblies. FIG. 4 is a control block diagram of a probe assembly in accordance with one embodiment of the present invention.

Referring to FIGS. 1 and 2, the ultrasound imaging apparatus 10 includes a probe assembly 100, a body 200, a display device 300, and an input device 400. The probe assembly 100 illustrated in FIG. 2 may correspond to one of first to fourth probe assemblies 100-1 to 100-4 illustrated in FIG. 1.

The probe assembly 100 transmits ultrasound waves to an object, receives echo ultrasound waves reflected from the object, and converts the echo ultrasound waves into an electrical signal (hereinafter referred to as an "ultrasound signal").

The ultrasound imaging apparatus 10 may include a plurality of probe assemblies 100. The plurality of probe assemblies 100 included in the ultrasound imaging apparatus 10 will be hereinafter described as first to fourth probe assemblies 100-1, 100-2, 100-3, and 100-4.

The body 200 forms an ultrasound image based on an ultrasound signal.

The body 200 may be a workstation connected to the first to fourth probe assemblies 100-1 to 100-4 and including the display device 300 and the input device 400.

The structure and operations of the probe assembly 100, e.g., one of the first to fourth probe assemblies 100-1 to 100-4, will be described below.

The probe assembly 100 includes a probe 110 that is directly in contact with an object, a probe connector 130 configured to transmit a signal to or receive a signal from the body 200, and a cable 120 configured to connect the probe 110 and the probe connector 130 with each other.

The probe 110 transmits ultrasound waves to or receives ultrasound waves from an object so as to obtain an ultrasound image of the inside of the object.

In detail, the probe 110 includes a transducer module 111 that converts an electric signal into vibration energy or vice versa. The transducer module 111 may transmit ultrasound waves to an object using a vibrator such as a piezoelectrics (not shown), and receive echo ultrasound waves reflected from the object.

When the number of such vibrators is, for example, 64 to 256, connecting members, the number of which is equal to the number of the vibrators are needed to connect the probe assembly 100 and the body 200.

Here, the object may be a living body of a human or an animal or a tissue in the living body, such as a blood vessel, a bone, a muscle, etc. but is not limited thereto. The type of the object is not limited provided that an image of an inner structure thereof can be obtained using the ultrasound imaging apparatus 10.

Referring to FIGS. 3A to 3C, according to the array of the transducer module 111, the probe 110 may be prepared as a linear probe having a linear surface as illustrated in FIG. 3A, prepared as a convex probe having a convex surface as illustrated in FIG. 3B, or prepared as a matrix probe as illustrated in FIG. 3C, but is not limited thereto. The probe 110 may be prepared as a different type probe which is well known in the art (such as a phased array probe, etc.) other than those illustrated in FIGS. 3A to 3C.

One end of the cable 120 may be connected to the probe 110, and another end of the cable 120 may be connected to the probe connector 130.

In accordance with an embodiment of the present invention, the probe connector 130 may be placed on the body 200 and automatically locked onto the body 200 through a locking mechanism.

The term 'locking' should be understood as including performing an access through a mechanical coupling between the probe connector 130 and the body 200 or controlling an access in a state in which the probe connector 130 and the body 200 have been mechanically coupled to each other. Here, 'locking' has a different meaning from mechanically placing the probe connector 130 on the body 200.

Figure 5:
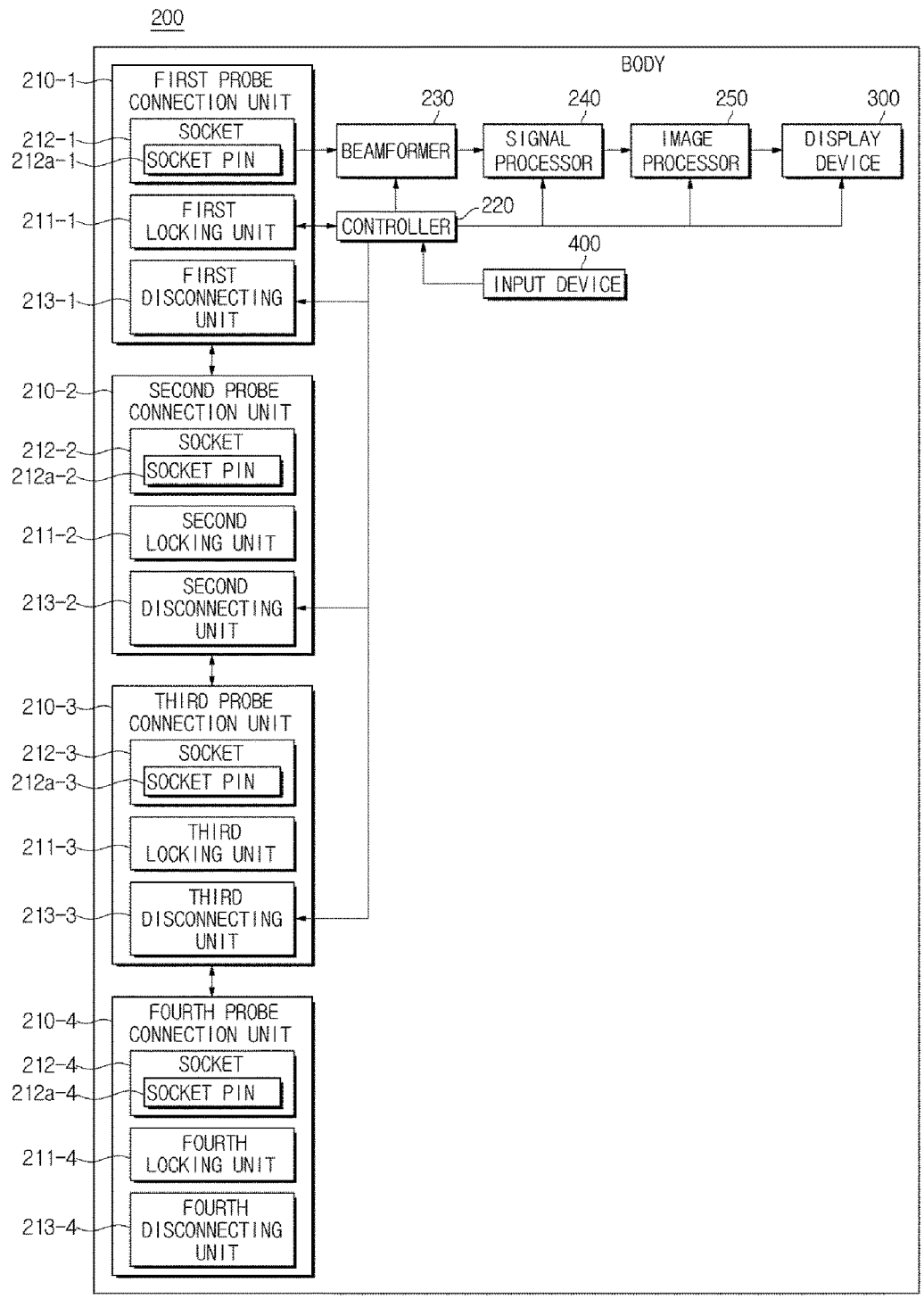
FIG. 5 is a control block diagram of a body in accordance with one embodiment of the present invention.

Locking should be understood as including locking performed to cause a probe signal transceiver 131 of the probe connector 130 to access to a body signal transceiver 212 of a probe connection unit 210 (see FIG. 5). Here, the "access" includes a contact access and a non-contact access.

Locking may be performed through a user's manual manipulation or automatically. For example, when the probe connection unit 210 includes an additional locking unit 211 (see FIG. 5), locking may be performed by driving the locking unit 211, as will be described in detail below.

The probe connector 130 may be embodied as an external connector to be coupled with the probe connection unit 210 of the body 200 which is embodied as an internal connector.

Referring to FIG. 4, the probe connector 130 in accordance with an embodiment of the present invention includes the probe signal transceiver 131 and a printed circuit board (PCB) 132.

When locking is performed, the probe signal transceiver 131 receives a control signal from the body signal transceiver 212 of the body 200 or transmits an ultrasound signal generated by the probe 110 to the body signal transceiver 212 of the body 200.

The probe signal transceiver 131 of the probe connector 130 may be embodied as a terminal with a conductive connection pin 131a to transmit or receive a control signal or an ultrasound signal in a contact manner, or may be embodied as a wireless communication module to transmit or receive a control signal or an ultrasound signal in a non-contact manner. Here, it is assumed that the probe signal transceiver 131 is such a terminal.

The terminal 131 may include the connection pin 131a to be inserted into a socket of the body 200. When locking is performed, the connection pin 131a may transmit an ultrasound signal to a socket pin 212a of the body 200 (see FIG. 5) or receive a control signal from the socket pin 212a while being in contact with the socket pin 212a.

When locking is performed, the PCB 132 receives a control signal from the body 200 or drives the probe assembly 100 based on a received control signal.

Also, when locking is performed, the PCB 132 may transmit an ultrasound signal generated by the probe 110 to the terminal 131.

The structure and operations of the body 200 will be described in detail with reference to FIG. 5 below.

FIG. 5 is a control block diagram of a body 200 in accordance with an embodiment of the present invention.

Referring to FIG. 5, the body 200 includes a plurality of probe connection units, e.g., first to fourth probe connection units 210-1 to 210-4, a controller 220, a beamformer 230, a signal processor 240, an image processor 250, a display device 300, and an input device 400.

Although FIG. 5 illustrates that the four probe connection units 210-1 to 210-4 are provided, for example, two, three, or five probe connection units may be provided on the body 200 according to the number of probe assemblies 100. That is, the number of the plurality of probe connection units is not limited to four as illustrated in FIG. 5.

Hereinafter, the probe connector 130 of the first probe assembly 100-1 placed in the first probe connection unit 210-1 will be referred to as the first probe connector 130-1, the probe connector 130 of the second probe assembly 100-2 placed in the second probe connection unit 210-2 will be referred to as the second probe connector 130-2, the probe connector 130 of the third probe assembly 100-3 placed in the third probe connection unit 210-3 will be referred to as the third probe connector 130-3, and the probe connector 130 of the fourth probe assembly 100-4 placed in the fourth probe connection unit 210-4 will be referred to as the fourth probe connector 130-4.

The first probe connection unit 210-1 may be automatically locked with the first probe connector 130-1 placed therein according to a control signal received from the controller 220.

The first probe connection unit 210-1 may be an internal connector.

The first probe connection unit 210-1 includes a first locking unit 211-1, a body signal transceiver 212-1, and a first disconnecting unit 213-1.

The first locking unit 211-1 locks the first probe connector 130-1 into the first probe connection unit 210-1 or unlocks the first probe connector 130-1 from the first probe connection unit 210-1 according to a control signal received from the controller 220.

In detail, when a user selects the first probe connection unit 210-1, the first locking unit 211-1 may cause a socket pin 212a-1 included in the body signal transceiver 212-1 to be in contact with the connection pin 131a of the first probe connector 130-1 so as to exchange an ultrasound signal and a control signal between the first probe assembly 100-1 and the body 200.

To this end, the first locking unit 211-1 may mechanically couple the first probe connector 130-1 placed in the first probe connection unit 210-1 and the first probe connection unit 210-1 to each other.

For example, the first locking unit 211-1 may include a rotary motor to rotationally insert the first probe connector 130-1 embodied as an external screw or bolt into a coupling groove of the first probe connection unit 210-1 embodied as an internal screw or nut.

Otherwise, the first locking unit 211-1 may be embodied as an electromagnet to be coupled with an electromagnet attached to the first probe connector 130-1 according to a control signal received from the controller 220.

In addition, the first locking unit 211-1 may include a linear actuator, a motor, etc. to mechanically couple the first probe connector 130-1 placed in the probe connection unit 210-1 to the probe connection unit 210-1, and may mechanically couple the first probe connector 130-1 and the first probe connection unit 210-1 to each other.

The first locking unit 211-1 may be omitted. In this case, a user may perform locking by manually coupling the first probe connector 130-1 to the first probe connection unit 210-1.

The body signal transceiver 212-1 may be embodied as a socket with the socket pin 212a-1 having a conductive property to transmit or receive a control signal or an ultrasound signal in a contact manner, or may be embodied as a wireless communication module to exchange a control signal or an ultrasound signal with the probe signal transceiver 131 of the first probe connector 130-1 in a non-contact manner. Here, it is assumed that the body signal transceiver 212-1 is embodied as such a socket.

The socket 212-1 may include the socket pin 212a-1 into which the connection pin 131a of the first probe connector 130-1 is inserted to be in contact with the connection pin 131a. The socket pin 212a-1 comes in contact with the connection pin 131a of the first probe connector 130-1 to transmit or receive an ultrasound signal of the first probe assembly 100-1 when the first probe connector 130-1 and the first probe connection unit 210-1 are locked with each other.

In accordance with an embodiment of the present invention, the socket pins 212a-1 to 212a-4 included in the respective probe connection units 210-1 to 210-4 are electrically connected to one another. For example, the socket pin 212a-1 of the first probe connection unit 210-1 among the probe connection units 210-1 to 210-4 is directly connected to the beamformer 230.

For example, when the socket pin 212a-1 of the first probe connection unit 210-1 is directly connected to the beamformer 230, the socket pin 212a-2 of the second probe connection unit 210-2 is connected between the socket pin 212a-1 of the first probe connection unit 210-1 and the socket pin 212a-3 of the third probe connection unit 210-3, the socket pin 212a-3 of the third probe connection unit 210-3 is connected between the socket pin 212a-2 of the second probe connection unit 210-2 and the socket pin 212a-4 of the fourth probe connection unit 210-4, and the socket pin 212a-4 of the fourth probe connection unit 210-4 may be directly connected to the socket pin 212a-3 of the third probe connection unit 210-3.

Here, that A is "directly connected to" B means that A and B are electrically connected to each other while any probe connection unit 210 is not present therebetween.

Also, that A and B are "electrically connected to" each other means that A and B are connected via a circuit, a bus, etc. to exchange an electric signal with each other.

That is, an ultrasound signal generated by the first probe assembly 100-1 may be transmitted to the beamformer 230 via the socket pin 212a-1 of the first probe connection unit 210-1, and an ultrasound signal generated by the second probe assembly 100-2 may be transmitted to the beamformer 230 via the socket pins 212a-2 and 212a-1 of the second probe connection unit 210-2 and the first probe connection unit 210-1.

Also, an ultrasound signal generated by the third probe assembly 100-3 may be transmitted to the beamformer 230 via the socket pins 212a-3, 212a-2, and 212a-1 of the third, second, and first probe connection units 210-3, 210-2, and 210-1. An ultrasound signal generated by the fourth probe assembly 100-4 may be transmitted to the beamformer 230 via the socket pins 212a-4, 212a-3, 212a-2, and 212a-1 of the fourth, third, second, and first probe connection units 210-4, 210-3, 210-2, and 210-1.

Although FIG. 5 illustrates that the four probe connection units 210-1 to 210-4 are connected in one direction, they may be connected in two directions, as will be described with reference to FIG. 10 below.

The first disconnecting unit 213-1 disconnects the first probe connection unit 210-1 and the second probe connection unit 210-2 from each other.

Hereinafter, that "an A probe connection unit and a B probe connection unit are connected to or disconnected from each other" means that "a socket of the A probe connection unit and a socket of the B probe connection unit are connected to or disconnected from each other".

The first disconnecting unit 213-1 may be embodied as, for example, an analog switch, a field-effect transistor (FET), an integrated circuit, micro-electromechanical systems (MEMS), etc. to disconnect the first probe connection unit 210-1 and the second probe connection unit 210-2 from each other.

In accordance with an embodiment of the present invention, the first disconnecting unit 213-1 may be embodied as a mechanical device to disconnect the first probe connection unit 210-1 and the second probe connection unit 210-2 from each other, as will be described with reference to FIGS. 8A to 10 below.

The second probe connection unit 210-2 may be also automatically locked with the second probe connector 130-2 placed therein according to a control signal received from the controller 220.

Similarly, the second probe connection unit 210-2 includes a second locking unit 211-2, a body signal transceiver 212-2, and a second disconnecting unit 213-2. The second locking unit 211-2 and the socket 212-2 are as described above with respect to the first probe connection unit 210-1 and are thus not described again here.

The second disconnecting unit 213-2 disconnects the second probe connection unit 210-2 and the third probe connection unit 210-3 from each other.

The second disconnecting unit 213-2 may be also embodied as an analog switch, a FET, an integrated circuit, MEMS, etc. or may be embodied as a mechanical device.

The third probe connection unit 210-3 may be automatically locked with the third probe connector 130-3 placed thereon according to a control signal received from the controller 220.

Similarly, the third probe connection unit 210-3 includes a third locking unit 211-3, a body signal transceiver 212-3, and a third disconnecting unit 213-3. The third locking unit 211-3 and the socket 212-3 are as described above with respect to the first probe connection unit 210-1 and are thus not described again here.

The third disconnecting unit 213-3 disconnects the third probe connection unit 210-3 and the fourth probe connection unit 210-4 from each other.

The fourth probe connection unit 210-4 may be automatically locked with the fourth probe assembly 100-4 placed thereon according to a control signal received from the controller 220.

Similarly, the fourth probe connection unit 210-4 includes a fourth locking unit 211-4, a body signal transceiver 212-4, and a fourth disconnecting unit 210-4. The fourth locking unit 211-4 and the body signal transceiver 212-4 are as described above with respect to the first probe connection unit 210-1 and are thus not described again here.

However, when a fifth probe connection unit (not shown) is not present, the fourth disconnecting unit 213-4 need not perform disconnection and receive a control signal from the controller 220. Thus, the fourth disconnecting unit 213-4 may be omitted.

The controller 220 controls overall operations of elements of the ultrasound imaging apparatus 10, e.g., the first to fourth probe connection units 210-1 to 210-4, the beamformer 230, the signal processor 240, the image processor 250, the display device 300, the probe assembly 100, etc.

In detail, when a command to select a probe assembly, e.g., the first probe assembly 100-1, among the first to fourth probe assemblies 100-1 to 100-4 is received from a user via the input device 400, the controller 220 controls the first locking unit 211-1 to automatically lock the first probe assembly 100-1 with the first probe connector 130-1.

In this case, the controller 220 controls the second to fourth probe connection units 210-2 to 210-4 (hereinafter referred to as non-via probe connection units) among the probe connection units 210-1 to 210-4 on the body 200 to be disconnected from the first probe connection unit 210-1.

The non-via probe connection units mean probe connection units forming a stub.

To this end, the controller 220 transmits a control signal to the first disconnecting unit 213-1 included in the selected first probe connection unit 210-1 so as to control the first disconnecting unit 213-1 to disconnect the first probe connection unit 210-1 and the second probe connection unit 210-2 from each other. As a result, the first probe connection unit 210-1 is disconnected from not only the second probe connection unit 210-2 but also the third and fourth probe connection units 210-3 and 210-4.

When a command to select the second probe assembly 100-2 is received via the input device 400, the controller 220 controls the second locking unit 211-2 to automatically lock the second probe assembly 100-2.

In this case, the controller 220 transmits a control signal to the second locking unit 211-2 so as to control the second locking unit 211-2 to lock the second probe connector 130-2 into the second probe connection unit 210-2.

Also, the controller 220 controls non-via probe connection units (i.e., the third and fourth probe connection units 210-3 and 210-4) to be disconnected from the second probe connection unit 210-2 among the probe connection units 210-1 to 210-4 on the body 200 except for a via probe connection unit (i.e., the first probe connection unit 210-1) connected between the beamformer 230 and the second probe connection unit 210-2.

To this end, the controller 220 transmits a control signal to the second disconnecting unit 213-2 included in the second probe connection unit 210-2 so as to control the second disconnecting unit 213-2 to disconnect the second probe connection unit 210-2 and the third probe connection unit 210-3 from each other. As a result, the second probe connection unit 210-2 is disconnected from not only the third probe connection unit 210-3 but also the fourth probe connection unit 210-4.

When a command to select the third probe assembly 100-3 is received from the input device 400, the controller 220 controls the third locking unit 211-3 to automatically lock the third probe assembly 100-3.

In this case, the controller 220 transmits a control signal to the third locking unit 211-3 so as to control the third locking unit 211-3 to lock the third probe connector 130-3 into the third probe connection unit 210-3.

Also, the controller 220 controls a non-via probe connection unit (i.e., the fourth probe connection unit 210-4) to be disconnected from the first probe connection unit 210-1 and the third probe connection unit 210-3 among the probe connection units 210-1 to 210-4 on the body 200 except for via probe connection units (i.e., the first and second probe connection units 210-1 and 210-2) that connect the controller 220 and the third probe connection unit 210-3.

To this end, the controller 220 transmits a control signal to the third disconnecting unit 213-3 included in the selected third probe connection unit 210-3 so as to control the third disconnecting unit 213-3 to disconnect the third probe connection unit 210-3 and the fourth probe connection unit 210-4 from each other.

Thus, the third probe connection unit 210-3 is disconnected from the fourth probe connection unit 210-4.

Also, when the fourth probe assembly 100-4 is selected by a user, the controller 220 controls the fourth locking unit 211-4 to perform automatic locking.

In this case, the controller 220 transmits a control signal to the fourth locking unit 211-4 so as to control the fourth locking unit 211-4 to lock the fourth probe connector 130-4 into the fourth probe connection unit 210-4.

When the fourth probe assembly 100-4 is selected, a non-via probe assembly is not present and thus a mechanism for performing disconnection is omitted.

Next, the controller 220 may transmit a control signal to the PCB 132 connected to the access in 131a of at least one locked probe connector (at least one among the probe connectors 130-1 to 130-4) to drive the probe assembly 100 corresponding to the at least one locked probe connector, receive an ultrasound signal from the probe assembly 100, or process or display various information obtained by the probe assembly 100.

Although not shown, the controller 220 may include a processor, a read-only memory (ROM) that stores a control program for controlling the ultrasound imaging apparatus 10, and a random access memory (RAM) that stores a signal or ultrasound image data received from the probe assembly 100 or the input device 400 of the ultrasound imaging apparatus 10 or that is used as a storage region corresponding to various operations performed by the ultrasound imaging apparatus 10.

Otherwise, a graphic processing board including a processor, a RAM, or a ROM may be included in an additional PCB electrically connected to the controller 220. The processor, the RAM, and the ROM may be connected via an internal bus.

Also, the controller 220 may be used as a term indicating a component that includes a processor, a RAM, and a ROM. Also, the controller 220 may be used as a term indicating a component that includes a processor, a RAM, a ROM, and a processing board.

The beamformer 230 is a device that delays transmitted ultrasound waves or received echo ultrasound waves for an appropriate time so that ultrasound waves generated by the probe 110 may be focused on a target point on an object at the same desired point of time or delayed time of echo ultrasound waves reflected from the target point on the object may be modified at the probe 110.

The beamformer 230 delays an ultrasound signal to be transmitted or received by a probe (at least one among the probes 110-1 to 110-4) included in at least one locked probe assembly (at least one among the probe assemblies 100-1 to 100-4).

The beamformer 230 may be included in the body 200 corresponding to a back end of the ultrasound imaging apparatus 10 as illustrated in FIG. 5 or included in the probe assembly 100 corresponding to a front end of the ultrasound imaging apparatus 10. However, exemplary embodiments of the beamformer 230 are not limited thereto. Although all or some of the elements of the beamformer 230 may be included in the front end or back end of the ultrasound imaging apparatus 10, it is assumed that the beamformer 230 is included in the body 200 for convenience of explanation.

In accordance with an embodiment of the present invention, the beamformer 230 is directly connected to the socket pin 212a-1 of the first probe connection unit 210-1. The beamformer 230 may exchange an ultrasound signal with the first probe assembly 100-1 via the socket pin 212a-1 of the first probe connection unit 210-1, exchange an ultra-sound signal with the second probe assembly 100-2 via the socket pins 212a-1 and 212a-2 of the first probe connection unit 210-1 and the second probe connection unit 210-2, exchange an ultrasound signal with the third probe assembly 100-3 via the socket pins 212a-1 to 212a-3 of the first to third probe connection units 210-1 to 210-3, and exchange an ultrasound signal with the fourth probe assembly 100-4 via the socket pins 212a-1 to 212a-4 of the first to fourth probe connection units 210-1 to 210-4.

The signal processor 240 converts a signal received from the beamformer 230 into a format appropriate for image processing. For example, the signal processor 240 may perform filtering to remove a noise signal other than a desired frequency band.

The signal processor 240 may be embodied as a digital signal processor (DSP), and generate ultrasound image data by performing envelope detection to detect the intensity of echo ultrasound waves, based on a signal received from the beamformer 230.

The image processor 250 generates an image based on the ultrasound image data generated by the signal processor 240 such that a user, e.g., a doctor or a patient, may visually check an object, e.g., the inside of a human body.

The image processor 250 transmits an ultrasound image generated from the ultrasound image data to the display device 300.

In one embodiment of the present invention, the image processor 250 may further perform additional image processing on the ultrasound image. For example, the image processor 250 may further perform image post-processing, e.g., may correct or readjust the contrast, brightness, or sharpness of the ultrasound image.

The additional image processing may be performed by the image processor 250 according to predetermined settings or an instruction or command received from a user via the input device 400.

The display device 300 may display the ultrasound image generated by the image processor 250 so that a user may visually check the inner structure of the object, a tissue included in the object, or the like.

The input device 400 receives an instruction or command to control the ultrasound imaging apparatus 10 from a user. The input device 400 may include a user interface, for example, a keyboard, a mouse, a trackball, a touch screen, a paddle, or the like.

The structures of and the relationship between a probe connector 130, i.e., one of the probe connectors 130-1 to 130-4, and a probe connection unit 210, i.e., one of the probe connection units 210-1 to 210-4, in accordance with an embodiment of the present invention will be described in more detail with reference to FIGS. 6 to 10 below.

Figure 6:
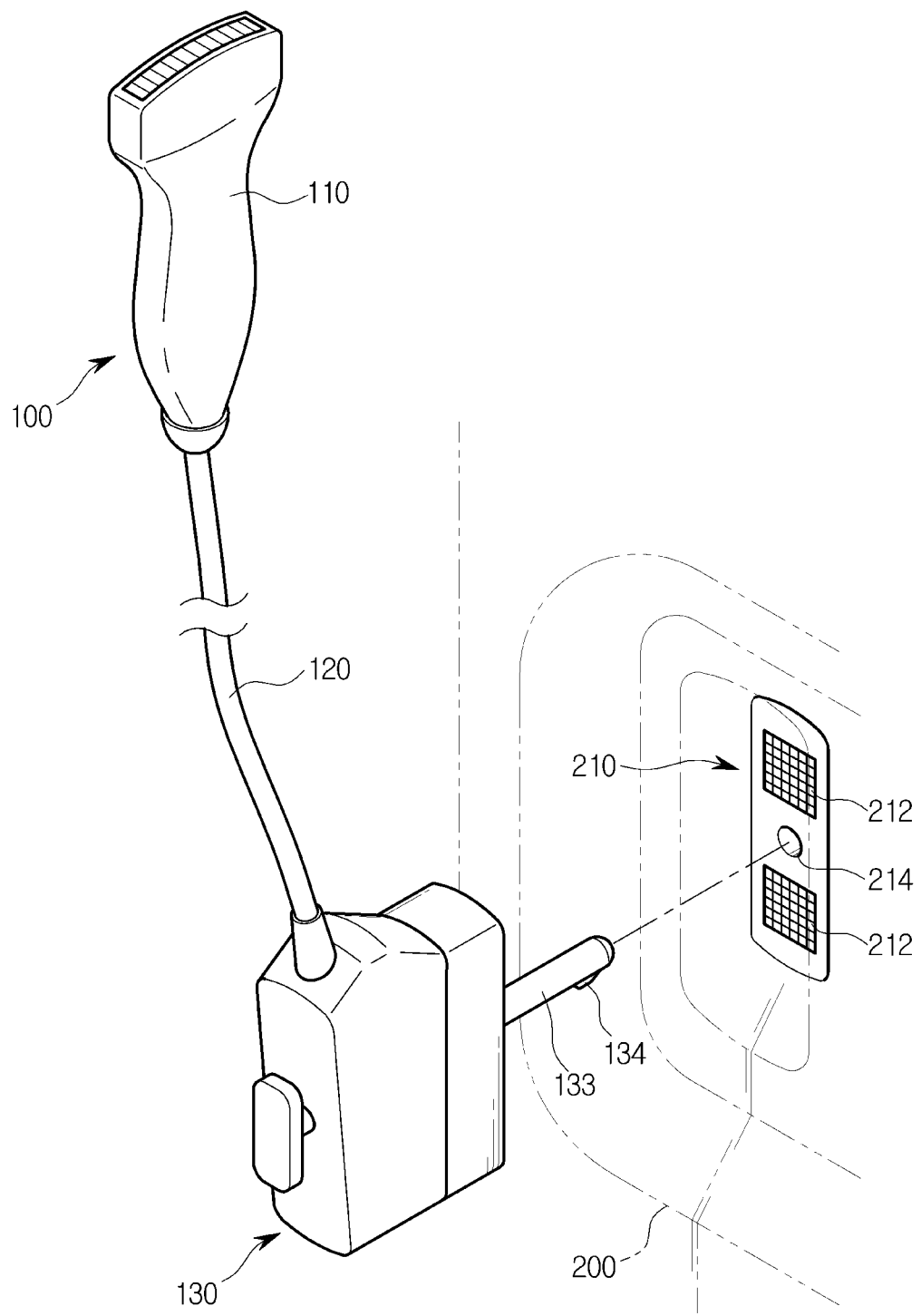
FIG. 6 is a front perspective view of the exteriors of a probe connector and a probe connection unit in accordance with one embodiment of the present invention.
Figure 7:
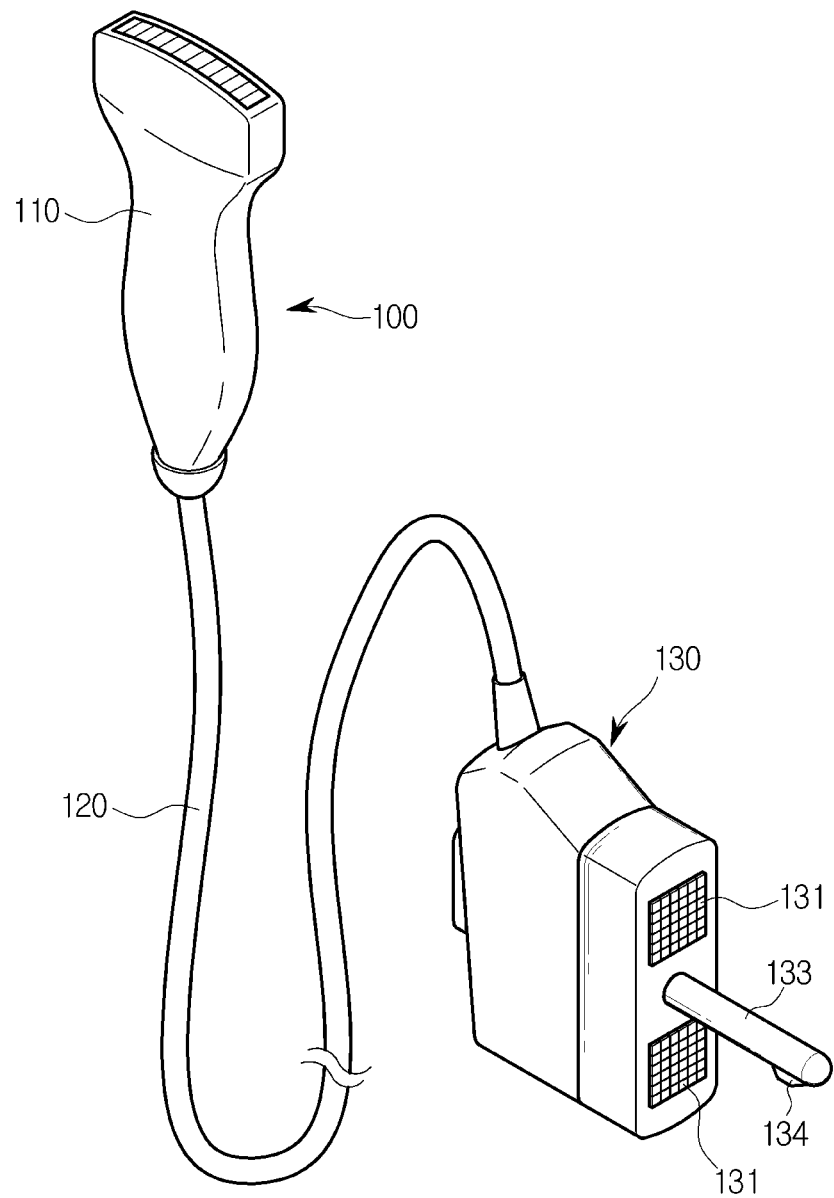
FIG. 7 is a rear perspective view of the exterior of a probe connector in accordance with one embodiment of the present invention.

However, the structures and shapes of the probe connector 130 and the probe connection unit 210 are not limited to those illustrated in FIGS. 6 and 7 and may be embodied variously.

FIG. 6 is a front perspective view of the exteriors of a probe connector 130 and a probe connection unit 210 in accordance with one embodiment of the present invention. FIG. 7 is a rear perspective view of the exterior of the probe connector 130 in accordance with one embodiment of the present invention.

Referring to FIGS. 6 and 7, the probe connector 130 may include a locking shaft 133 protruding from the inside of the probe connector 130 to the outside of the probe connector 130 so as to mechanically place the probe connector 130 in the probe connection unit 210 of the body 200, and a locking member 134 for locking the probe connector 130 and the probe connection unit 210 with each other.

In the probe connection unit 210, a coupling groove 214 in which the locking shaft 133 is placed may be formed. In this case, the locking unit 211 may be embodied as a motor so as to rotate the locking shaft 133 placed in the coupling groove 214 such that the probe connection unit 210 and the probe connector 130 are coupled to each other.

In detail, a user may place the probe connector 130 in the probe connection unit 210 by inserting the locking shaft 133 into the coupling groove 214 of the probe connection unit 210. In this case, the terminal 131 of the probe connector 130 may be inserted into the socket 212 of the body 200.

However, since the connection pin 131a provided on the terminal 131 of the probe connector 130 and the socket pin 212a provided on the socket 212 of the body 200 are not complete in contact with each other through mechanical "placement", the probe connector 130 is not electrically connected to the probe connection unit 210. Thus, "locking" should be performed to electrically connect the probe connector 130 and the probe connection unit 210.

To this end, the locking member 134 may be provided on the locking shaft 133 and the locking shaft 133 may be rotated by the motor included in the locking unit 211 to place the locking member 134 into a locking groove (not shown) of the probe connection unit 210. Thus, the probe connector 130 and the probe connection unit 210 may be locked with each other.

That is, as the probe connector 130 is placed into the probe connection unit 210, the terminal 131 is inserted into the socket 212 and the probe connector 130 and the probe connection unit 210 are locked with each other. Thus, the connection pin 131a comes in contact with the socket pin 212a of the socket 212, so that a control signal of the body 200 may be input to a plurality of connection pins 131a or an ultrasound signal may be transmitted to the body 200.

Although it has been described that the locking unit 211 includes the motor for rotating the locking shaft 133 of the probe connector 130 placed in the coupling groove 214 so as to perform locking, embodiments of the present invention are not limited thereto and locking may be performed by various means capable of automatically coupling the probe connector 130 to the probe connection unit 210 according to a control signal.

For example, locking may be performed by forming the probe connector 130 in the form of an external screw or bolt to be inserted into the probe connection unit 210 and to be coupled to the probe connection unit 210 embodied as an internal screw or nut, as a rotary motor rotates.

The probe connector 130 may further include an electromagnet to be locked with the probe connection unit 210 that also includes an electromagnet.

A method of disconnecting a probe connection unit 210 which is a non-via probe connection unit and a probe connection unit 210 of the probe assembly 100 selected by a user through a disconnecting unit 213, e.g., one of the first to third disconnecting units 213-1 to 213-3, will be described with reference to FIGS. 8A to 10 below.

Figure 8A:
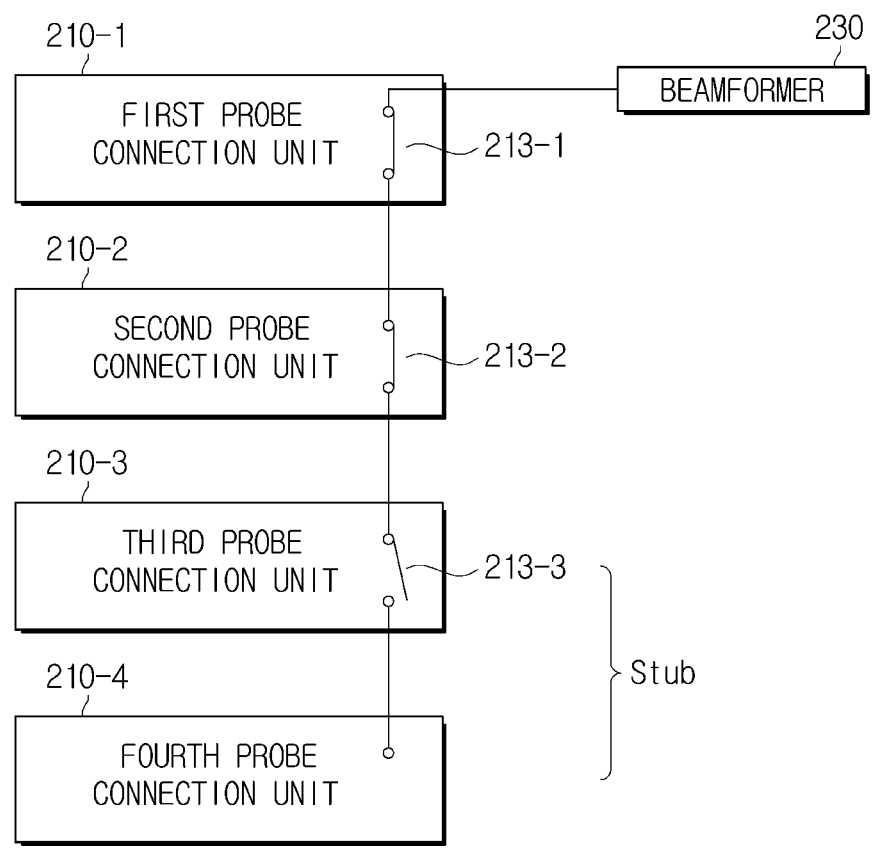
FIGS. 8A and 8B are conceptual diagrams illustrating disconnecting methods in accordance with embodiments of the present invention.
Figure 8B:
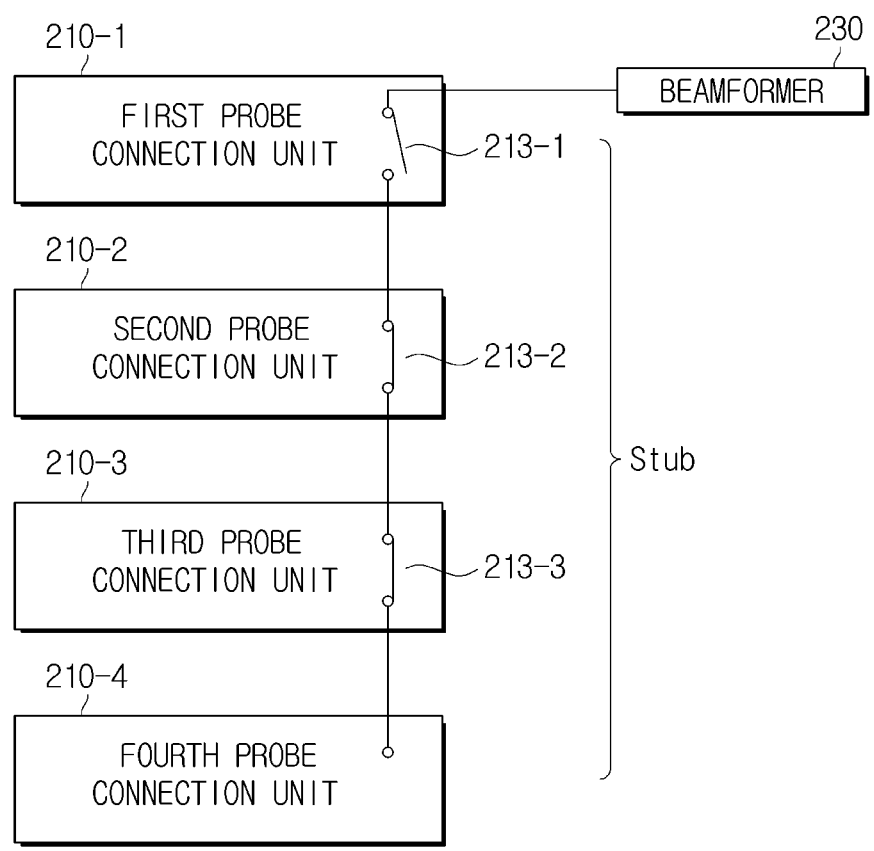

FIGS. 8A and 8B are conceptual diagrams illustrating disconnecting methods in accordance with embodiments of the present invention.

Referring to FIG. 8A, for example, when a user selects the third probe assembly 100-3, the third disconnecting unit 213-3 included in the third probe connection unit 210-3 in accordance with an embodiment of the present invention may disconnect the third probe connection unit 210-3 and the fourth probe connection unit 210-4 from each other.

Thus, a stub caused by a transmission line of the fourth probe connection unit 210-4 may be removed.

Referring to FIG. 8B, when a user selects, for example, the first probe assembly 100-1, the first disconnecting unit 213-1 included in the first probe connection unit 210-1 in accordance with an embodiment of the present invention may also disconnect the first probe connection unit 210-1 and the second probe connection unit 210-2 from each other.

The second disconnecting unit 213-2 included in the second probe connection unit 210-2 may also disconnect the second probe connection unit 210-2 and the third probe connection unit 210-3 from each other.

Thus, a stub caused by transmission lines of the second to fourth probe connection units 210-2 to 210-4 may be removed.

Figure 8C:
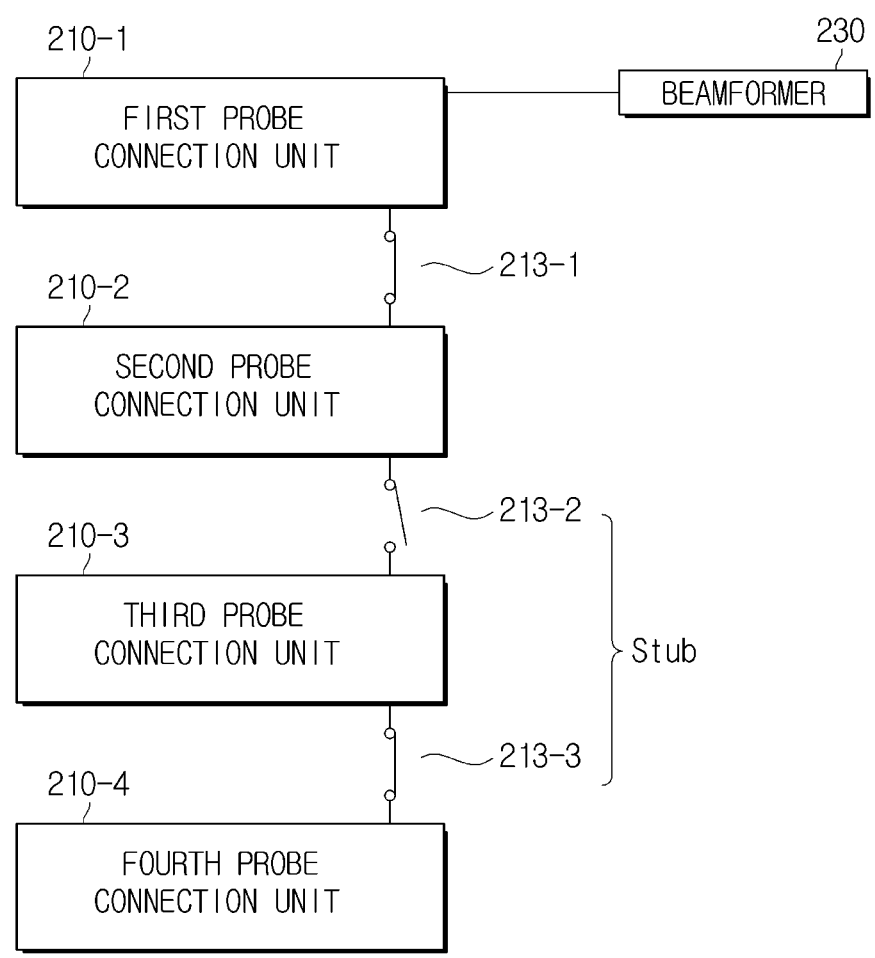
FIGS. 8C and 8D are conceptual diagrams illustrating disconnecting methods in accordance with other embodiments of the present invention.
Figure 8D:
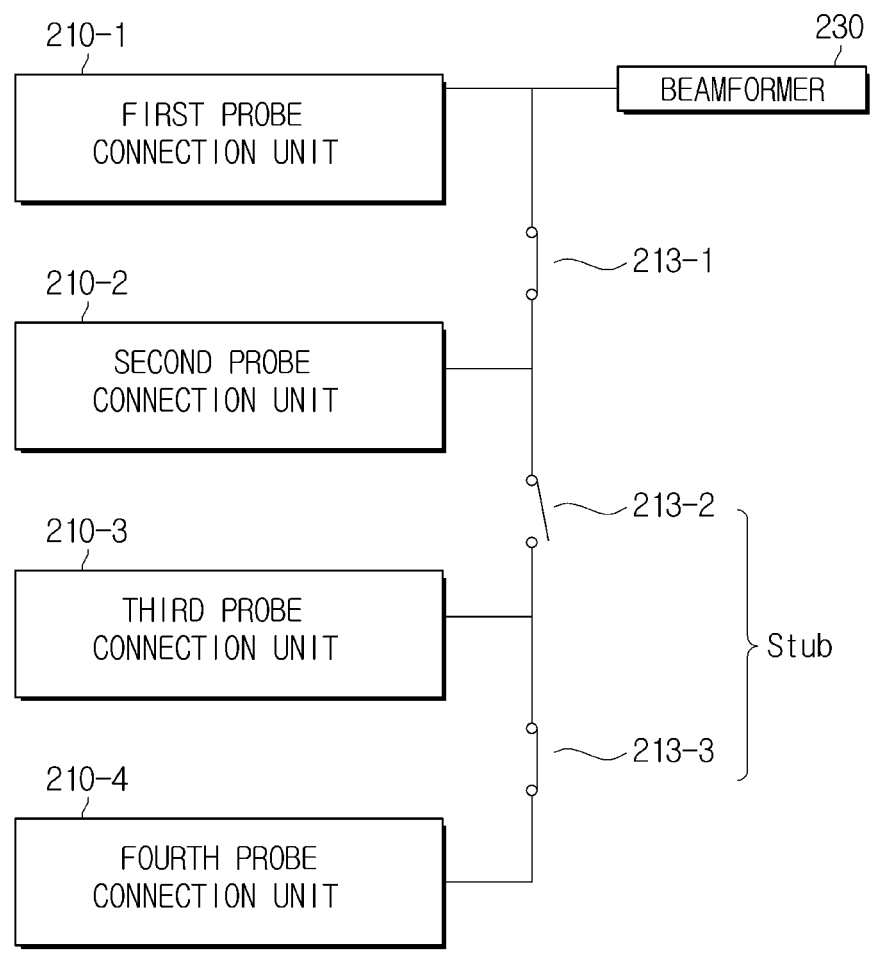

A disconnecting method in accordance with an embodiment of the present invention is not, however, limited to those of FIGS. 8A and 8B. FIGS. 8C and 8D are conceptual diagrams illustrating disconnecting methods in accordance with other embodiments of the present invention.

Referring to FIG. 8C, the first disconnecting unit 213-1 that disconnects the first probe connection unit 210-1 and the second probe connection unit 210-2 may be installed outside the first probe connection unit 210-1, the second disconnecting unit 213-2 that disconnects the second probe connection unit 210-2 and the third probe connection unit 210-3 may be installed outside the second probe connection unit 210-2, and the third disconnecting unit 213-3 that disconnects the third probe connection unit 210-3 and the fourth probe connection unit 210-4 may be installed outside the third probe connection unit 210-3.

For example, when a user selects the second probe assembly 100-2, the second disconnecting unit 213-2 installed outside the second probe connection unit 210-2 in accordance with an embodiment of the present invention may disconnect the second probe connection unit 210-2 and the third probe connection unit 210-3 from each other.

Thus, a stub caused by transmission lines of the third and fourth probe connection units 210-3 and 210-4 may be removed.

Referring to FIG. 8D, the first disconnecting unit 213-1 that disconnects the first probe connection unit 210-1 and the second probe connection unit 210-2 may be installed outside the first probe connection unit 210-1, the second disconnecting unit 213-2 that disconnects the second probe connection unit 210-2 and the third probe connection unit 210-3 may be installed outside the second probe connection unit 210-2, and the third disconnecting unit 213-3 that disconnects the third probe connection unit 210-3 and the fourth probe connection unit 210-4 may be installed outside the third probe connection unit 210-3. In this case, the first disconnecting unit 213-1 may disconnect not only the first probe connection unit 210-1 and the second probe connection unit 210-2 but also the beamformer 230 and the second probe connection unit 210-2, the second disconnecting unit 213-2 may disconnect not only the second probe connection unit 210-2 and the third probe connection unit 210-3 but also the first disconnecting unit 213-1 and the third probe connection unit 210-3, and the third disconnecting unit 213-3 may disconnect not only the third probe connection unit 210-3 and the fourth probe connection unit 210-4 but also the second disconnecting unit 213-2 and the fourth probe connection unit 210-4.

For example, when a user selects the second probe assembly 100-2, the second disconnecting unit 213-2 installed outside the second probe connection unit 210-2 in accordance with an embodiment of the present invention may disconnect the second probe connection unit 210-2 and the third probe connection unit 210-3 and disconnect the first disconnecting unit 213-1 and the third probe connection unit 210-3.

Thus, a stub caused by transmission lines of the third and fourth probe connection units 210-3 and 210-4 may be removed.

Figure 9A:
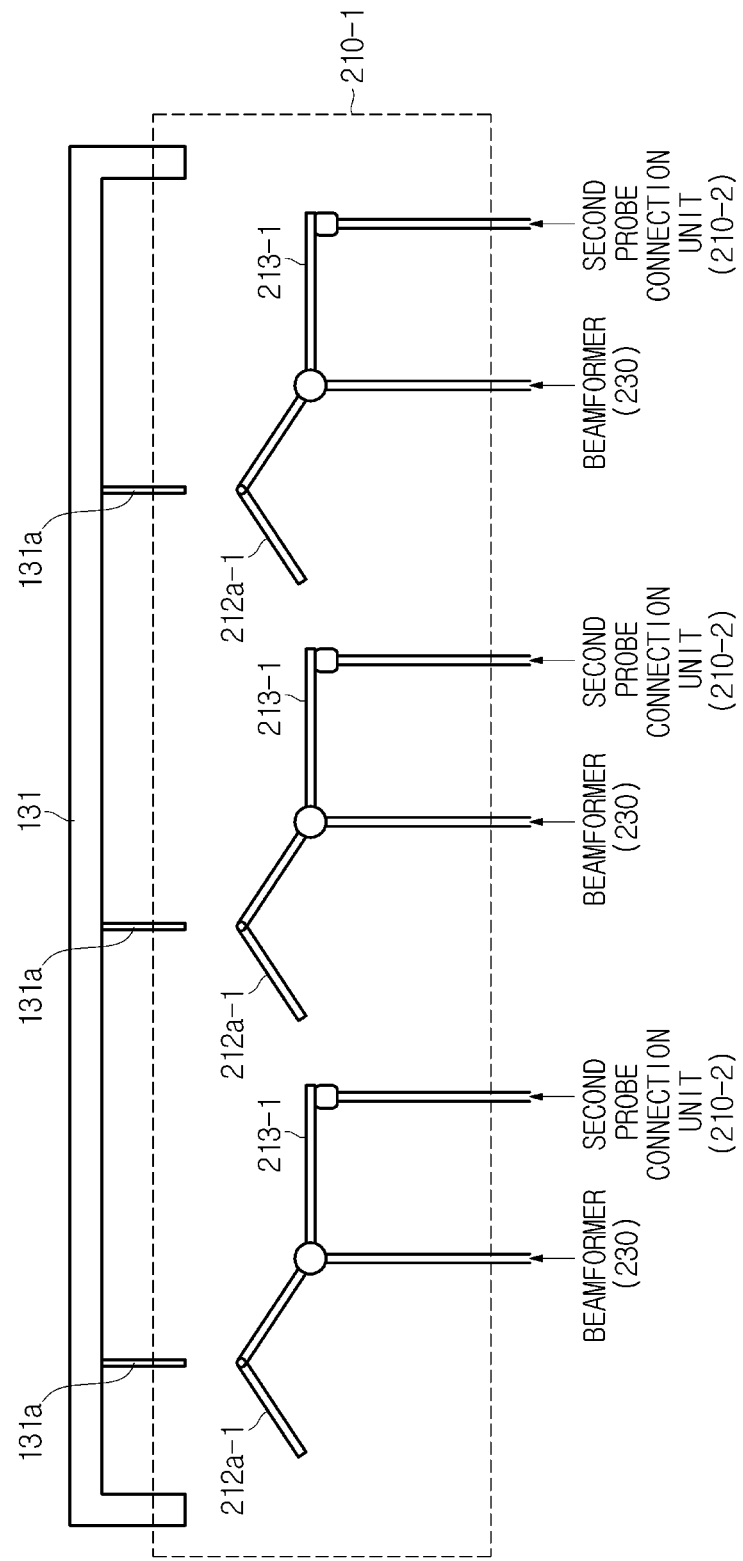
FIGS. 9A and 9B illustrate probe connection units that include a disconnecting unit embodied as a mechanical device in accordance with embodiments of the present invention.
Figure 9B:
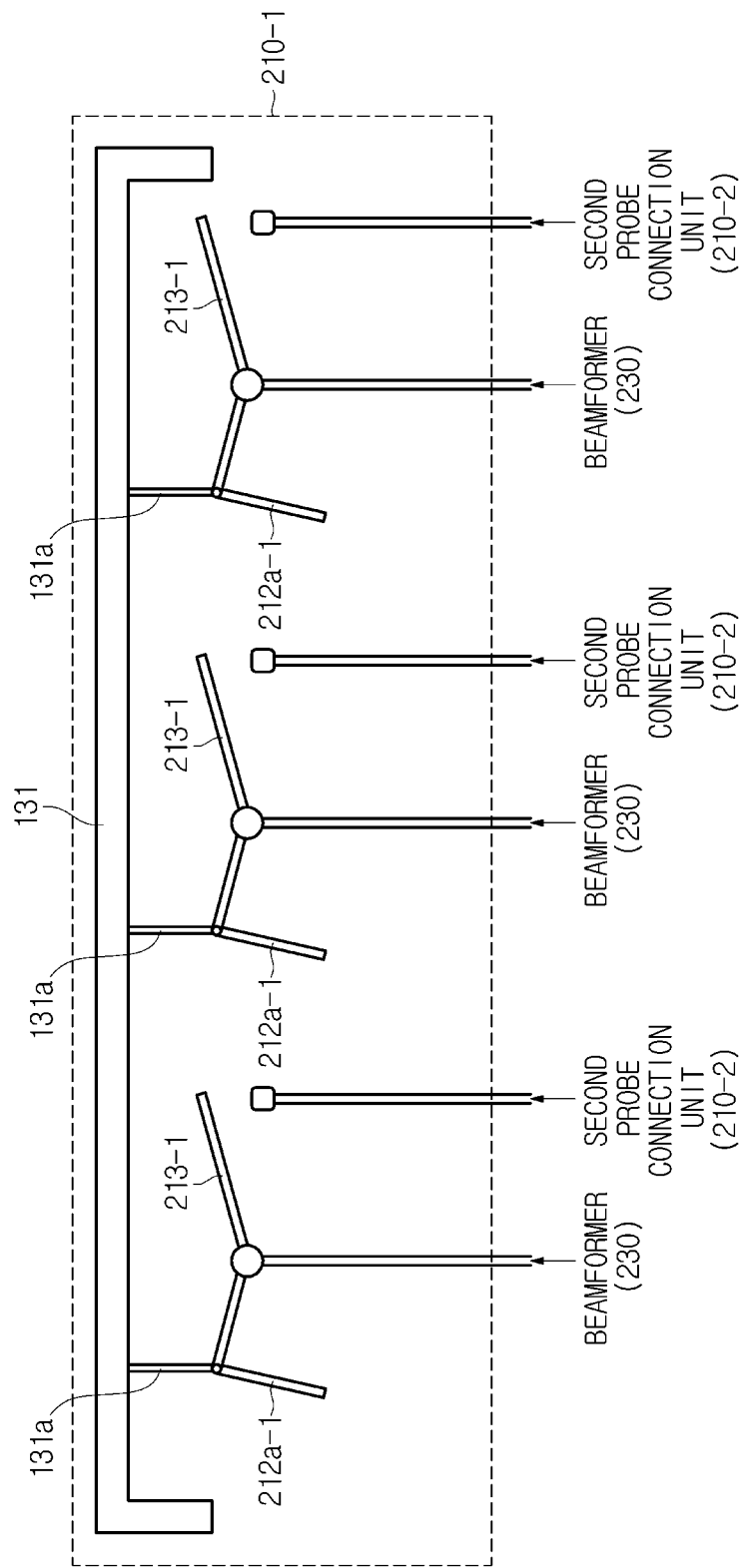

FIGS. 9A and 9B illustrate probe connection units that include a disconnecting unit such as that shown in FIG. 8A or 8B which is embodied as a mechanical device in accordance with embodiments of the present invention. The embodiments of the FIGS. 9A and 9B will be described with respect to the first probe connection unit 210-1 and the first probe connector 130-1 below Referring to FIG. 9A, a socket pin 212a-1 of a first probe connection unit 210-1 in accordance with an embodiment of the present invention may have a convex shape, and may be connected to a beamformer 230 and a first disconnecting unit 213-1 having a conductive property.

The first disconnecting unit 213-1 may be connected to the socket pin 212a-1, the beamformer 230, and the second probe connection unit 210-2, and may be disconnected from the second probe connection unit 210-2 according to the principle of a lever when a physical force is applied onto a top convex surface of the socket pin 212a-1 due to insertion of the connection pin 131a of the first probe connector 130-1 into the socket pin 212a-1.

Referring to FIG. 9B, when the connection pin 131a of the first probe connector 130-1 is inserted to be in contact with the socket pin 212a-1 due to locking of the first probe connector 130-1, a physical force is applied to the top convex surface of the socket pin 212a-1 and thus the first disconnecting unit 213-1 is disconnected from the second probe connection unit 210-2 according to the principle of the lever.

In accordance with another embodiment of the present invention, a physical force may be applied not only when the connection pin 131a is inserted due to locking but also when an additional driving device (e.g., a linear actuator, a motor, etc.) is operated to cause the socket pin 212a-1 and the first disconnecting unit 213-1 to protrude toward the connection pin 131a. In this case, the additional driving device may apply a physical force according to a control signal received from the controller 220.

Although FIGS. 9A and 9B illustrate three socket pins 212a-1 and three disconnecting units 213-1, the first probe connection unit 210-1 may include one or more socket pins 212a-1 and one or more disconnecting units 213-1. Thus, when the first probe connector 130-1 is locked, one or more connection pins 131a of the first probe connector 130-1 may be inserted to be in contact with one or more socket pins 212a-1.

Although not shown, the socket pin 212a-2 of the second probe connection unit 210-2 may also have a convex shape and be connected to the first probe connection unit 210-1 and the second disconnecting unit 213-2.

However, the second disconnecting unit 213-2 of the second probe connection unit 210-2 may be connected to the socket pin 212a-2 and the first probe connection unit 210-1, and may be connected to or disconnected from the third probe connection unit 210-3 according to a physical force applied to the socket pin 212a-2.

The socket pin 212a-3 of the third probe connection unit 210-3 may also have a convex shape, and be connected to the second probe connection unit 210-2 and the third disconnecting unit 213-3.

However, the third disconnecting unit 213-3 of the third probe connection unit 210-3 may be connected to the socket pin 212a-3 and the third probe connection unit 210-3, and may be connected to or disconnected from the fourth probe connection unit 210-4 according to a physical force applied to the socket pin 212a-3.

Figure 10A:
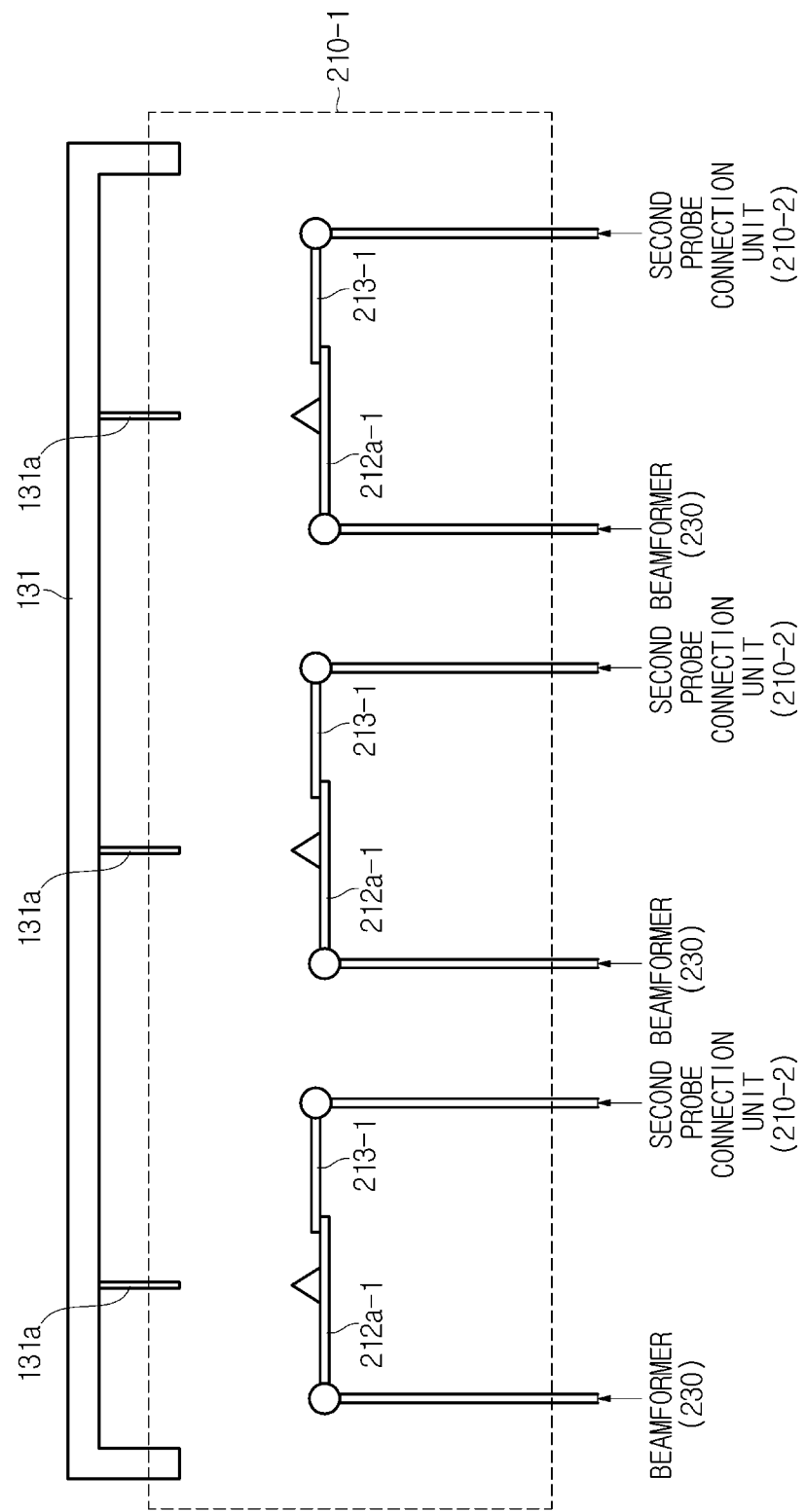
FIGS. 10A and 10B illustrate probe connection units that include a disconnecting unit embodied as a mechanical device in accordance with other embodiments of the present invention.
Figure 10B:
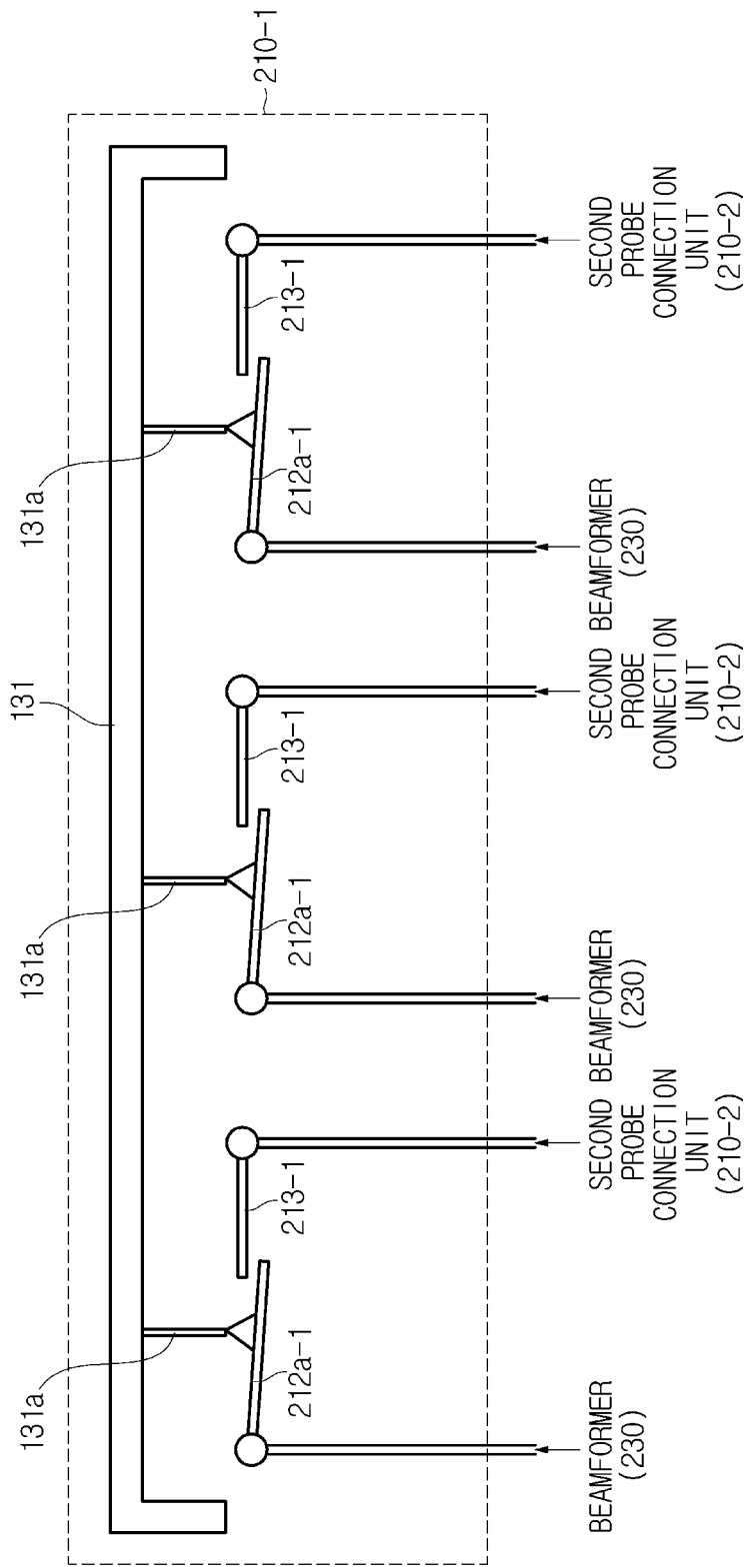

FIGS. 10A and 10B illustrate probe connection units that include a disconnecting unit such as that shown in FIG. 8A or 8B which is embodied as a mechanical device in accordance with other embodiments of the present invention. Similarly, the embodiments of the FIGS. 10A and 10B will be described with respect to the first probe connection unit 210-1 and the first probe connector 130-1 below.

Referring to FIG. 10A, a socket pin 212a-1 of a first probe connection unit 210-1 in accordance with another embodiment of the present invention has a convex portion. One end of the socket pin 212a-1 is connected to the beamformer 230, and the socket pin 212a-1 may be connected to the first disconnecting unit 213-1 when another end of the socket pin 212a-1 comes in contact with a bottom surface of the first disconnecting unit 213-1.

One end of the first disconnecting unit 213-1 is connected to the second probe connection unit 210-2, and the first disconnecting unit 213-1 may be connected to the socket pin 212a-1 when the socket pin 212a-1 comes in contact with another bottom end of the first disconnecting unit 213-1.

Referring to FIG. 10B, when the first probe connector 130-1 is locked to insert an connection pin 131a of the first probe connector 130-1 to be in contact with the socket pin 212a-1, a physical force is applied to the socket pin 212a-1 to cause the socket pin 212a-1 to be separated from the first disconnecting unit 213-1, thereby disconnecting the first disconnecting unit 213-1 from the second probe connection unit 210-2. In this case, in accordance with another embodiment of the present invention, a physical force may be applied not only when the connection pin 131a is inserted due to the locking of the first probe connector 130-1 but also when an additional driving device (e.g., a linear actuator, a motor, etc.) is operated to cause the socket pin 212a-2 and the first disconnecting unit 213-1 to protrude toward the connection pin 131a.

Although FIGS. 10A and 10B illustrate three socket pins 212a-1 and three disconnecting units 213-1, the first probe connection unit 210-1 may include one or more socket pins 212a-1 and one or more disconnecting units 213-1. Thus, when the first probe connector 130-1 is locked, one or more connection pins 131a of the first probe connector 130-1 may be inserted to be in contact with one or more socket pins 212a-1.

Although not shown, the socket pin 212a-2 of the second probe connection unit 210-2 may include a convex portion and be connected to the first probe connection unit 210-1. Also, the socket pin 212a-2 may be also connected to the second disconnecting unit 213-2 when the socket pin 212a-2 comes in contact with a bottom surface of the second disconnecting unit 213-2.

The second disconnecting unit 213-2 included in the second probe connection unit 210-2 is connected to the third probe connection unit 210-3 and may be also connected to the socket pin 212a-2 when the socket pin 212a-2 comes in contact with a bottom surface of the second disconnecting unit 213-2.

Similarly, when the connection pin 131a of the second probe connector 130-2 comes in contact with the socket pin 212a-2, a physical force is applied to the socket pin 212a-2 to cause the socket pin 212a-2 to be separated from the second disconnecting unit 213-2, thereby disconnecting the second disconnecting unit 213-2 from the third probe connection unit 210-3.

Similarly, the socket pin 212a-3 of the third probe connection unit 210-3 may have a convex portion and be connected to the second probe connection unit 210-2. Also, the socket pin 212a-3 may be connected to the third disconnecting unit 213-3 when the socket pin 212a-3 comes in contact with a bottom surface of the third disconnecting unit 213-3.

The third disconnecting unit 213-3 of the third probe connection unit 210-3 is connected to the fourth probe connection unit 210-4, and may be also connected to the socket pin 212a-3 when the socket pin 212a-3 comes in contact with the bottom surface of the third disconnecting unit 213-3.

Similarly, when the connection pin 131a of the third probe connector 130-3 comes in contact with the socket pin 212a-3, a physical force may be applied to the socket pin 212a-3 to cause the socket pin 212a-3 to be separated from the third disconnecting unit 213-3, thereby disconnecting the third disconnecting unit 213-3 from the fourth probe connection unit 210-4.

Meanwhile, since the fourth probe connection unit 210-4 need not include a disconnecting unit, the structure of the fourth probe connection unit 210-4 is not limited to those of the first to third probe connection units 210-1 to 210-3 of FIGS. 9A to 10B.

FIGS. 9A to 10B illustrate structures in which the first to fourth probe connection units 210-1 to 210-4 are connected in one direction, but the first to fourth probe connection units 210-1 to 210-4 in accordance with another embodiment of the present invention may be connected in two directions.

As described above, when the first to fourth probe connection units 210-1 to 210-4 are connected in two directions, the first probe connection unit 210-1 is directly connected to the beamformer 230 and the second probe connection unit 210-2, the second probe connection unit 210-2 is directly connected to the first probe connection unit 210-1 and the third probe connection unit 210-3, the third probe connection unit 210-3 is directly connected to the second probe connection unit 210-2 and the fourth probe connection unit 210-4, and the fourth probe connection unit 210-4 is directly connected to the third probe connection unit 210-3.

When the first to fourth probe connection units 210-1 to 210-4 are connected in one direction, the first probe connection unit 210-1 is connected to the beamformer 230 via one transmission line and is connected to the second probe connection unit 210-2 via one transmission line.

However, when the first to fourth probe connection units 210-1 to 210-4 are connected in two directions, the first probe connection unit 210-1 may be i) connected to the beamformer 230 via a plurality of transmission lines and connected to the second probe connection unit 210-2 via one transmission line, ii) connected to the beamformer 230 via one transmission line and connected to the second probe connection unit 210-2 via a plurality of transmission lines, or iii) connected to the beamformer 230 via a plurality of transmission lines and connected to the second probe connection unit 210-2 via a plurality of transmission lines.

Similarly, when the first to fourth probe connection units 210-1 to 210-4 are connected in one direction, the second probe connection unit 210-2 is connected to the first probe connection unit 210-1 via one transmission line and connected to the third probe connection unit 210-3 via one transmission line.

However, when the first to fourth probe connection units 210-1 to 210-4 are connected in two directions, the second probe connection unit 210-2 may be i) connected to the first probe connection unit 210-1 via a plurality of transmission lines and connected to the third probe connection unit 210-3 via one transmission line, ii) connected to the first probe connection unit 210-1 via one transmission line and connected to the third probe connection unit 210-3 via a plurality of transmission lines, or iii) connected to the first probe connection unit 210-1 via a plurality of transmission lines and connected to the third probe connection unit 210-3 via a plurality of transmission lines.

Similarly, when the first to fourth probe connection units 210-1 to 210-4 are connected in one direction, the third probe connection unit 210-3 is connected to the second probe connection unit 210-2 via one transmission line and connected to the fourth probe connection unit 210-4 via one transmission line.

However, when the first to fourth probe connection units 210-1 to 210-4 are connected in two directions, the third probe connection unit 210-3 may be i) connected to the second probe connection unit 210-2 via a plurality of transmission lines and connected to the fourth probe connection unit 210-4 via one transmission line, ii) connected to the second probe connection unit 210-2 via one transmission line and connected to the fourth probe connection unit 210-4 via a plurality of transmission lines, or iii) connected to the second probe connection unit 210-2 via a plurality of transmission lines and connected to the fourth probe connection unit 210-4 via a plurality of transmission lines.

The fourth probe connection unit 210-4 may be connected to the third probe connection unit 210-3 via one transmission line when the first to fourth probe connection units 210-1 to 210-4 are connected in one direction, and connected to the third probe connection unit 210-3 via a plurality of transmission lines When the first to fourth probe connection units 210-1 to 210-4 are connected in two directions.

Figure 11A:
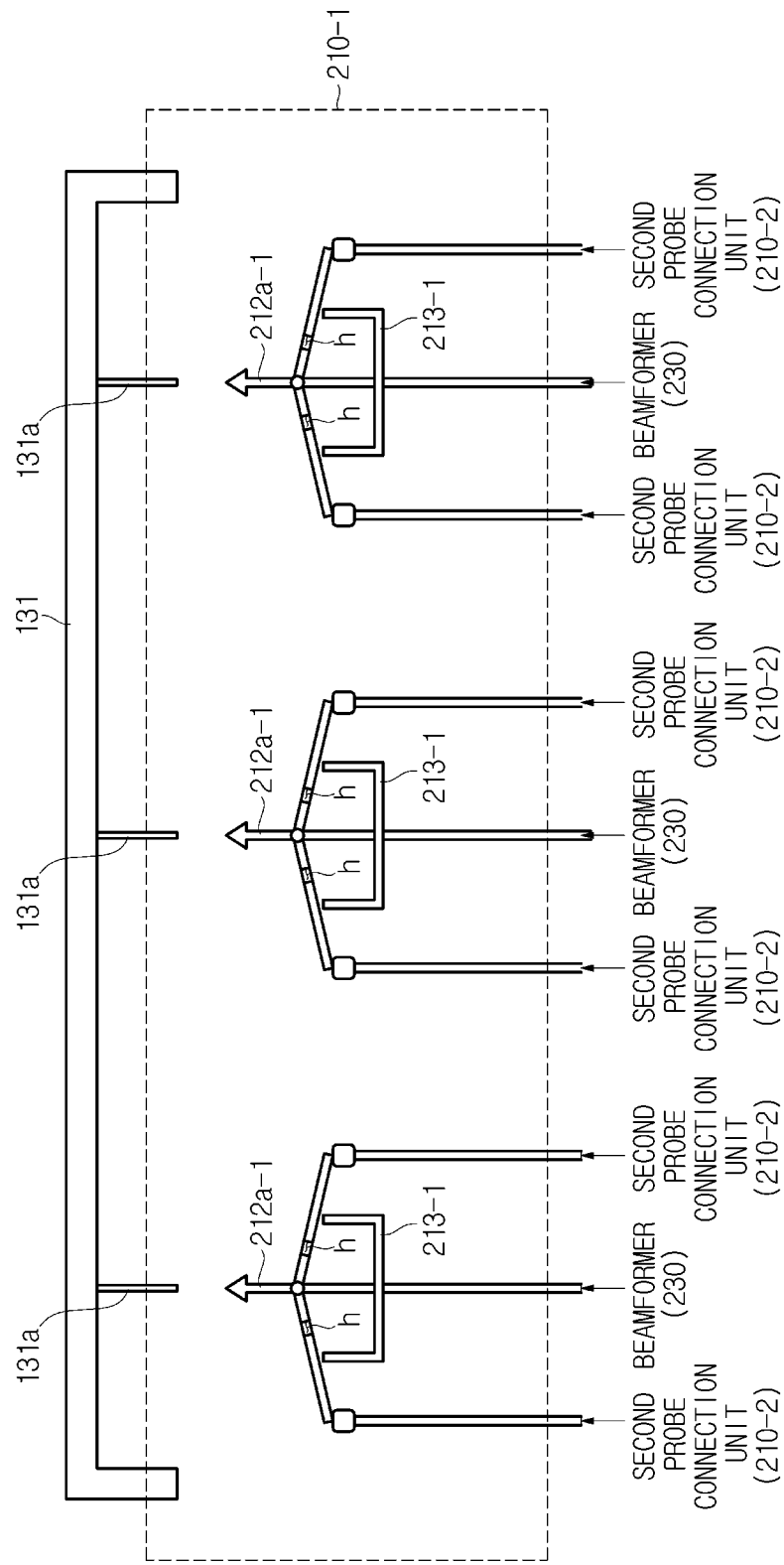
FIGS. 11A to 11C illustrate probe connection units that include a disconnecting unit embodied as a mechanical device and that are connected to one another in two directions in accordance with embodiments of the present invention.
Figure 11B:
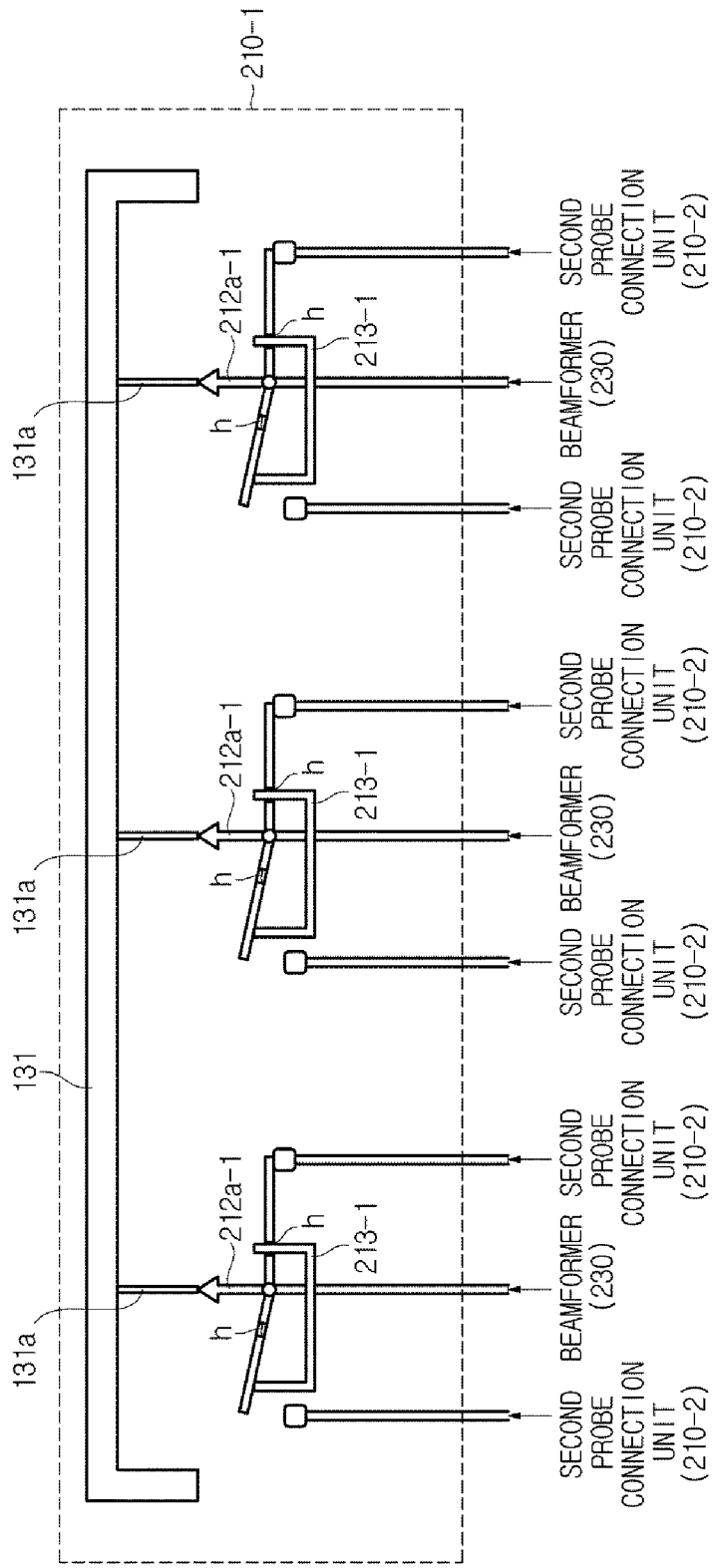
Figure 11C:
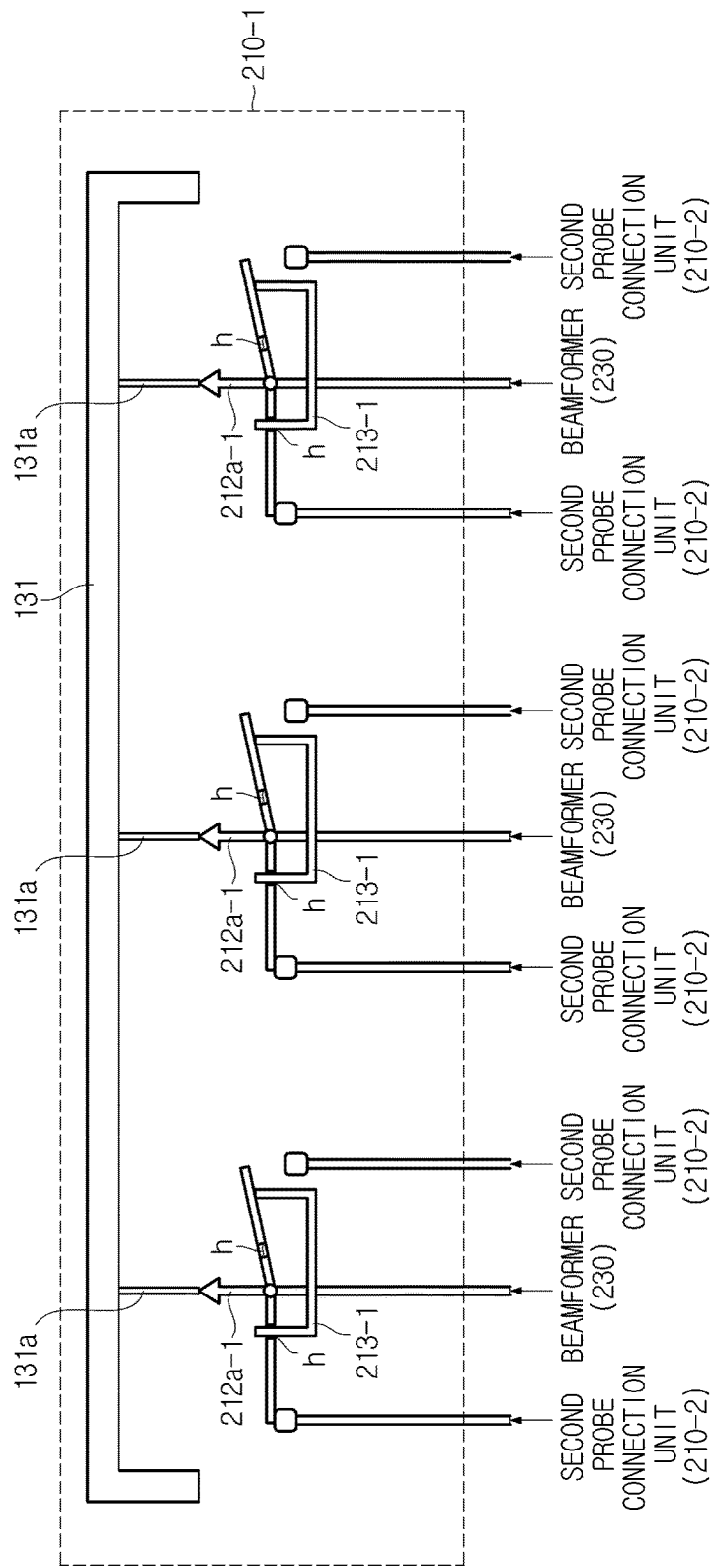

FIGS. 11A to 11C illustrate probe connection units that include a disconnecting unit embodied as a mechanical device and that are connected to one another in two directions in accordance with embodiments of the present invention. The embodiments of FIGS. 11A to 11C will be described with respect to a first probe connection unit 210-1 connected to the beamformer 230 via one transmission line and connected to the second probe connection unit 210-2 via two transmission lines, and a first probe connector 130-1 placed in the first probe connection unit 210-1.

Referring to FIG. 11A, a socket pin 212a-1 of the first probe connection unit 210-1 according to another embodiment of the present invention may have a central protruding portion and a central end thereof may be connected to one transmission line connected to a beamformer 230.

Also, both ends of the socket pin 212a-1 may be in contact with upper surfaces of two transmission lines connected to the second probe connection unit 210-2, respectively, to be electrically connected to the second probe connection unit 210-2.

A hole h is formed in both ends of the socket pin 212a-1, through which one end of the first disconnecting unit 213-1 may pass.

The first disconnecting unit 213-1 may include a rectangular shaped mechanical device without a sideline, and an additional driving device (not shown) such as a motor or a linear actuator for automatically transferring the first disconnecting unit 213-1 according to a control signal received from the controller 220.

Also, the first disconnecting unit 213-1 may include an additional manual device for moving the rectangular shaped mechanical device without the sideline to the left or the right, instead of the driving device. In this case, the rectangular shaped mechanical device without the sideline may be moved to the left or the right through a user's manual manipulation.

The first disconnecting unit 213-1 configured to be moved to the left or right according to a control signal received from the controller 220 will be described below.

One or both ends of the rectangular shaped mechanical device without the sideline may pass through the hole h in the socket pin 212a-1 as the rectangular shaped mechanical device without the sideline is moved to the left or the right.

Referring to FIG. 11B, when locking is performed, a central portion of the—rectangular shaped mechanical device without the sideline comes in contact with the connection pin 131a, and the driving device of the first disconnecting unit 213-1 may move the rectangular shaped mechanical device without the sideline to the left according to a control signal received from the controller 220.

In this case, a right end of the rectangular shaped mechanical device without the sideline passes through the hole h formed in a right end of the socket pin 212a-1 and a left end of the rectangular shaped mechanical device without the sideline separates a left end of the socket pin 212a-1 from a transmission line of the second probe connection unit 210-2. As a result, the left end of the socket pin 212a-1 may be disconnected from the transmission line of the second probe connection unit 210-2 and the right end of the socket pin 212a-1 may be electrically connected to the transmission line of the second probe connection unit 210-2 and a transmission line of the beamformer 230.

Referring to FIG. 11C, when locking is performed, the driving device of the first disconnecting unit 213-1 may move the rectangular shaped mechanical device without the sideline to the right according to a control signal received from the controller 220.

In this case, the left end of the mechanical device passes through the hole h formed in the left end of the socket pin 212a-1, and the right end of the mechanical device separates the right end of the socket pin 212a-1 from the transmission line of the second probe connection unit 210-2. As a result, the right end of the socket pin 212a-1 may be disconnected from the transmission line of the second probe connection unit 210-2 and the left end of the socket pin 212a-1 may be electrically connected to the transmission line of the second probe connection unit 210-2 and the transmission line of the beamformer 230.

That is, a direction in which the second probe connection unit 210-2 and the first probe connection unit 210-1 are disconnected from each other may vary according to a control signal received from the controller 220.

Although not shown, a socket pin 212a-2 of the second probe connection unit 210-2 may also have a central protruding portion and a central end thereof may be connected to a transmission line connected to the first probe connection unit 210-1.

When both ends of the socket pin 212a-2 come in contact with top surfaces of two transmission lines connected to the third probe connection unit 210-3, respectively, the socket pin 212a-2 may be also electrically connected to the third probe connection unit 210-3. A hole h may be formed in both ends of the socket pin 212a-2, through which the second disconnecting unit 213-2 may pass.

The second disconnecting unit 213-2 may also have a rectangular shaped mechanical device without a sideline, and an additional driving device or manual device, such as a motor or a linear actuator, which is configured to move the second disconnecting unit 213-2.

Similarly, the socket pin 212a-3 of the third probe connection unit 210-3 may have a central protruding portion and a central end thereof may be connected to a transmission line connected to the second probe connection unit 210-2.

When both ends of the socket pin 212a-3 come in contact with top surfaces of two transmission lines connected to the fourth probe connection unit 210-4, respectively, the socket pin 212a-3 may be electrically connected to the fourth probe connection unit 210-4. A hole h may be formed in both ends of the socket pin 212a-3, through which the third disconnecting unit 213-3 may pass.

The third disconnecting unit 213-3 may also have a rectangular shaped mechanical device without a sideline, and an additional driving device or manual device, such as a motor or a linear actuator, which is configured to move the third disconnecting unit 213-3.

The structures and operations of the socket pins 212a-2 and 212a-3 and the disconnecting units 213-1 and 213-2 of the second probe connection unit 210-2 and the third probe connection unit 210-3 are as described above with respect to the first probe connection unit 210-1 and are thus not described here again.

Since the fourth probe connection unit 210-4 need not include a disconnecting unit, the structure of the fourth probe connection unit 210-4 is not limited to those of the first to third probe connection units 210-1 to 210-3 illustrated in FIGS. 11A to 11C.

Although FIGS. 11A to 11C each illustrate one socket pin 212a-1, a plurality of socket pins 212a-1 may be present and a plurality of connection pins 131a may come in contact with the plurality of socket pins 212a-1.

Although the first to third disconnecting unit 213-1 to 213-3 included in the first to third probe connection units 210-1 to 210-3 have been described above, the first to third disconnecting units 213-1 to 213-3 may be installed outside the first to third probe connection units 210-1 to 210-3.

Figure 12:
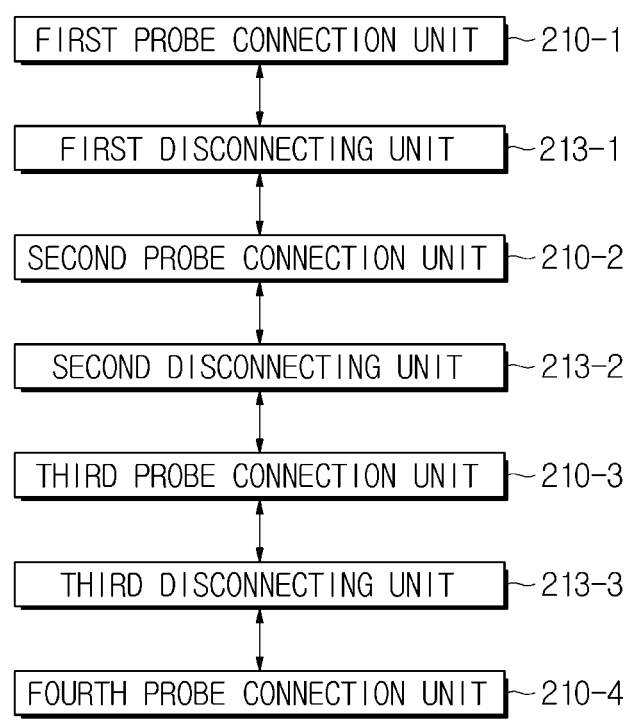
FIG. 12 is a conceptual diagram illustrating a disconnecting unit installed outside a probe connection unit in accordance with another embodiment of the present invention.

FIG. 12 is a conceptual diagram illustrating a disconnecting unit installed outside a probe connection unit in accordance with another embodiment of the present invention. FIG. 12 is another embodiment of FIG. 8C or 8D.

Referring to FIG. 12, a first disconnecting unit 213-1 which disconnects a first probe connection unit 210-1 and a second probe connection unit 210-2 is installed outside the first probe connection unit 210-1, a second disconnecting unit 213-2 which disconnects the second probe connection unit 210-2 and a third probe connection unit 210-3 is installed outside the second probe connection unit 210-2, and a third disconnecting unit 213-3 which disconnects the third probe connection unit 210-3 and a fourth probe connection unit 210-4 is installed outside the third probe connection unit 210-3.

However, all the first to third disconnecting units 213-1 to 213-3 may be included in the body 200, and embodied as an analog switch, a FET, an integrated circuit, MEMS, or a mechanical device.

The first disconnecting unit 213-1 embodied as a mechanical device will now be described as an example of a disconnecting unit 213 corresponding to one of the first to third disconnecting unit 213-1 to 213-3.

Figure 13A:
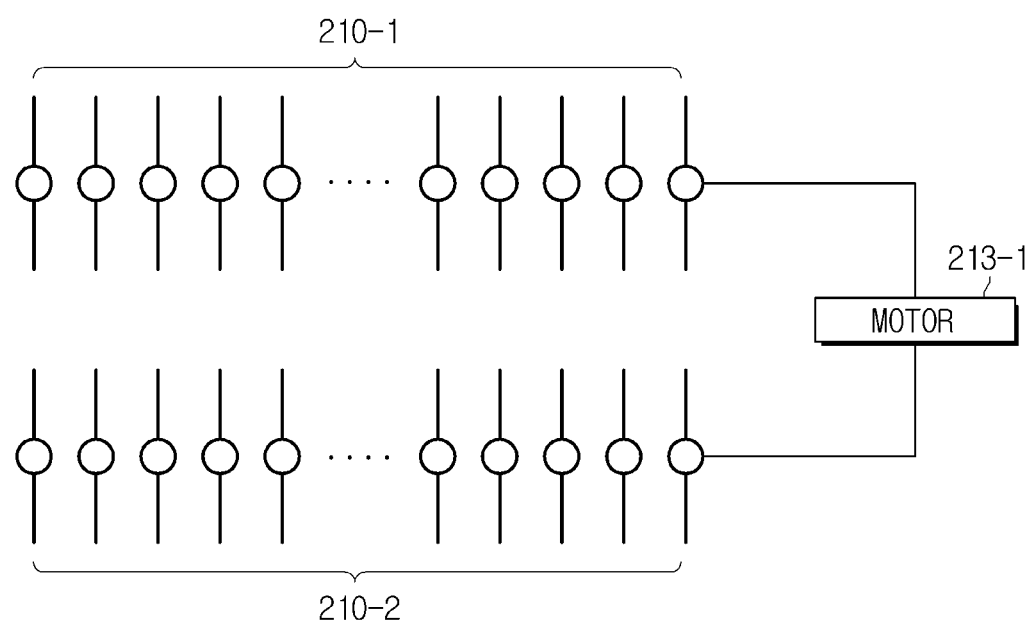
FIGS. 13A and 13B illustrate a probe connection unit that includes a first disconnecting unit installed outside a first probe connection unit in accordance with one embodiment of the present invention.
Figure 13B:
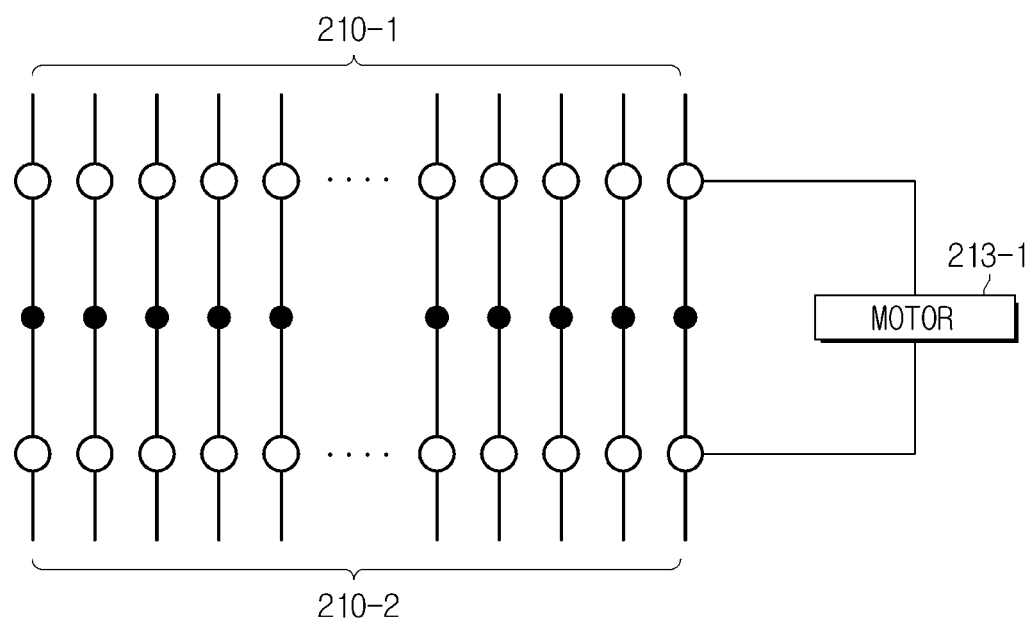
Figure 14A:
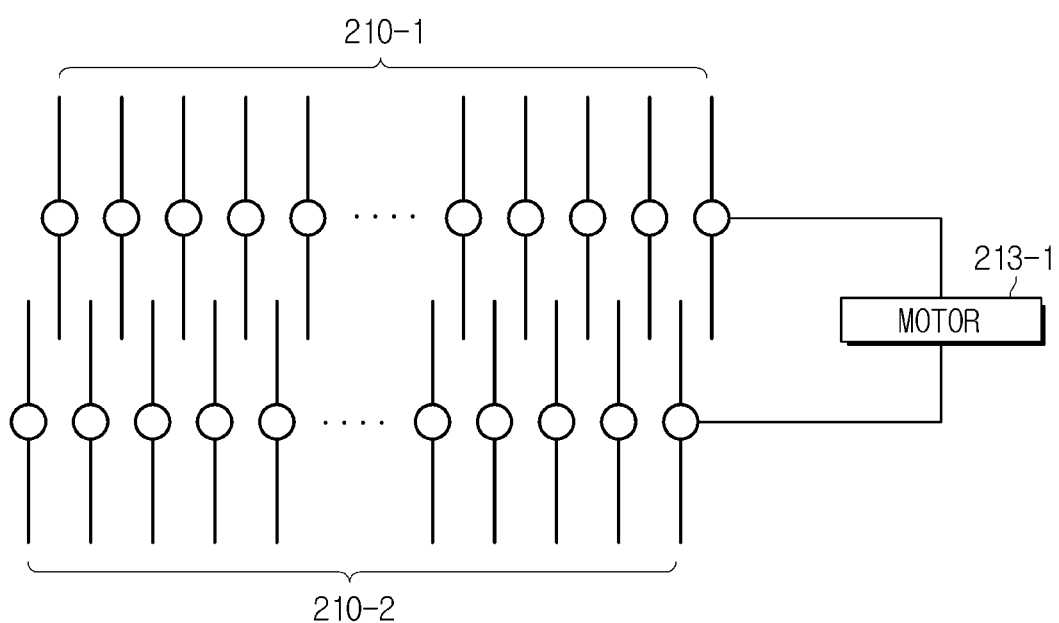
FIGS. 14A and 14B illustrate a probe connection unit that includes a first disconnecting unit installed outside a first probe connection unit in accordance with another embodiment of the present invention.
Figure 14B:
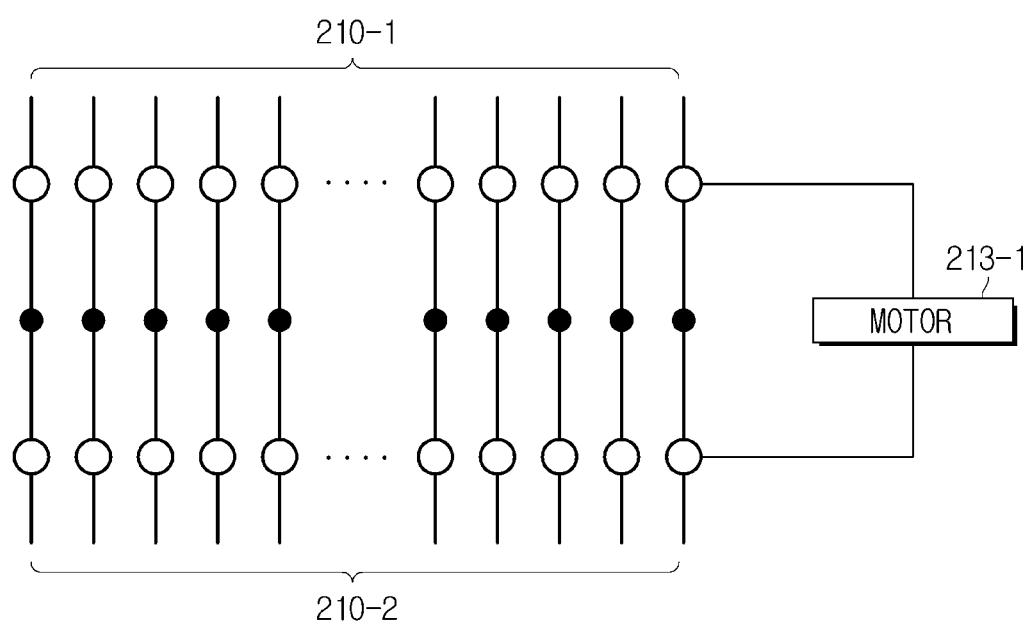

FIGS. 13A and 13B illustrate a probe connection unit that includes a first disconnecting unit installed outside a first probe connection unit in accordance with another embodiment of the present invention. FIGS. 13A and 13B are other embodiments of FIG. 12. FIGS. 14A and 14B illustrate a probe connection unit that includes a first disconnecting unit installed outside a first probe connection unit in accordance with another embodiment of the present invention. FIGS. 14A and 14B are other embodiments of FIG. 12.

Referring to FIGS. 13A and 13B, a first disconnecting unit 213-1 in accordance with an embodiment of the present invention may be a driving device that vertically moves at least one transmission line connected to the first probe connection unit 210-1 and at least one transmission line connected to the second probe connection unit 210-2 to be separated from each other (see FIG. 13A) or to be attached to each other (see FIG. 13B).

To this end, the first disconnecting unit 213-1 may be embodied as a motor or a linear actuator.

For example, when a user selects the first probe assembly 100-1, the controller 220 may transmit a control signal to the first disconnecting unit 213-1 to separate the first probe connection unit 210-1 and the second probe connection unit 210-2 from each other.

Referring to FIGS. 14A and 14B, a first disconnecting unit 213-1 in accordance with another embodiment of the present invention may be a driving device that moves at least one transmission line connected to the first probe connection unit 210-1 and at least one transmission line connected to the second probe connection unit 210-2 to the left or the right to be separated from each other (see FIG. 13A) or to be attached to each other (see FIG. 13B).

Similarly, in this case, the first disconnecting unit 213-1 may be embodied as a motor or a linear actuator.

In addition, the first to third disconnecting units 213 may be disconnected from the probe connection units 210-1 to 210-4 or the beamformer 230 in various ways and thus disconnecting means are not limited to that as described above.

Figure 15:
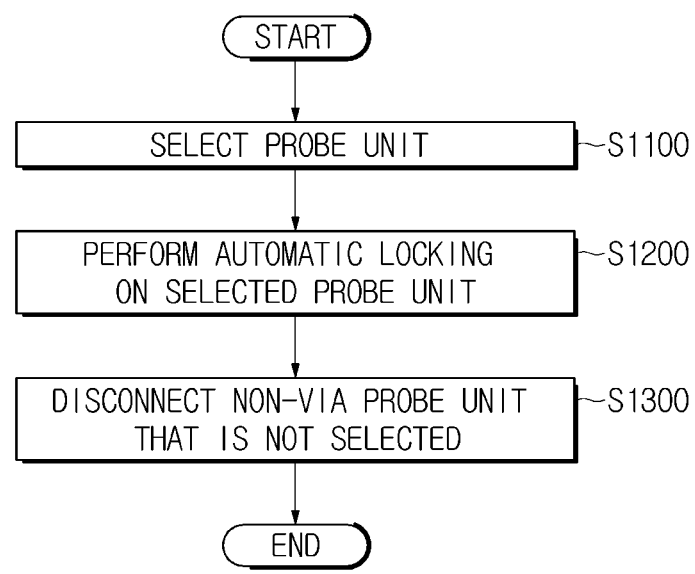
FIG. 15 is a flowchart of a method of controlling an ultrasound imaging apparatus in accordance with one embodiment of the present invention.

FIG. 15 is a flowchart of a method of controlling an ultrasound imaging apparatus in accordance with one embodiment of the present invention.

In accordance with one embodiment of the present invention, an ultrasound imaging apparatus includes a plurality of probe connection units in which a plurality of probe assemblies are placed, respectively.

For example, when four probe connection units are provided in the ultrasound imaging apparatus, a first probe connection unit is directly connected to a beamformer of the ultrasound imaging apparatus and a second probe connection unit, the second probe connection unit is directly connected to the first probe connection unit and a third probe connection unit, the third probe connection unit is directly connected to the second probe connection unit and a fourth probe connection unit, and the fourth probe connection unit is directly connected to the third probe connection unit.

An ultrasound signal transmitted or received by the beamformer with respect to the second probe connection unit is transmitted via the first probe connection unit. An ultrasound signal transmitted or received by the beamformer with respect to the third probe connection unit is transmitted via the first probe connection unit and the second probe connection unit. An ultrasound signal transmitted or received by the beamformer with respect to the fourth probe connection unit is transmitted via the first to third probe connection units.

A method of controlling the ultrasound imaging apparatus will be described below.

First, an input device receives a command to select one of a plurality of probe assemblies from a user (operation S1100).

Next, for automatically locking the selected probe assembly, a controller transmits a control signal to a locking unit of a probe connection unit in which the selected probe assembly is placed, and the locking unit receiving the control signal locks the selected probe assembly (operation S1200).

In contrast, in order to be continuously electrically connected to the selected probe assembly and to unlock non-selected probe assemblies in a state in which a plurality of probe assemblies have been already locked, the controller may transmit a control signal to locking units of probe connection units in which the non-selected probe assemblies are placed and the locking units receiving the control signal may unlock the non-selected probe assemblies.

A method of performing locking and unlocking is as described above and is thus not described here.

Next, the controller controls a non-via probe connection unit to be disconnected from the probe connection unit in which the selected probe assembly is placed (operation S1300).

Here, a via probe connection unit means a probe connection unit via which a signal is exchanged between the beamformer and the probe connection unit corresponding to the selected probe assembly. For example, when a third probe assembly is selected, via probe connection units are the first and second probe connection units.

Here, the non-via probe connection unit means a probe connection unit among probe connection units corresponding to non-selected probe assemblies except for a via probe connection unit. For example, when the third probe assembly is selected, the fourth probe connection unit is a non-via probe connection unit.

For disconnection, the ultrasound imaging apparatus may further include disconnecting units inside or outside a plurality of probe connection units. The disconnecting units may be embodied as, for example, analog switches, FETs, integrated circuits, MEMS, mechanical devices, etc., and disconnect probe connection units from each other.

For example, when a first probe assembly is selected, the controller may transmit a control signal to a first disconnecting unit so as to disconnect the first probe connection unit and the second probe connection unit. When a second probe assembly is selected, a control signal may be transmitted to a second disconnecting unit so as to disconnect the second probe connection unit and the third probe connection unit. When the third probe assembly is selected, a control signal may be transmitted to a third disconnecting unit so as to disconnect the third probe connection unit and the fourth probe connection unit. However, when a fourth probe assembly is selected, non-via probe connection units are not present and thus the process of transmitting a control signal described above may be omitted.

Meanwhile, the first to fourth disconnecting units may be disconnected through a user's manual manipulation and need not thus be disconnected according to a control signal received from the controller.

The disconnecting units are as described above and are not described again here.

Although referring to FIG. 15, the selected probe assembly is automatically locked and then non-via probe assemblies that are not selected are disconnected, embodiments of the present invention are not limited to the order and the selected probe assembly may be automatically locked after the non-via probe assemblies that are not selected are disconnected (operation S1300).

As is apparent from the above description, in an ultrasound imaging apparatus and a method of controlling the same in accordance with one embodiment of the present invention, a non-selected probe connector is disconnected to decrease the length of a stub which is a short branch line connected in parallel to a transmission line.

Also, according to the embodiments set forth herein, in an ultrasound imaging apparatus and a method of controlling the same in accordance with one aspect, a non-selected probe connector is disconnected to decrease negative effects due to signal attenuation caused by an impedance of an unnecessary transmission line.

The above methods of controlling an ultrasound imaging apparatus can be embodied as computer readable code in a computer readable medium. The computer readable medium may be any recording apparatus capable of storing data that is read by a computer system, e.g., a read-only memory (ROM), a random access memory (RAM), a magnetic tape, a magnetic disk, a flash memory, an optical data storage device, and so on. The computer readable medium can be distributed among computer systems that are interconnected through a computer communication network, and the present invention may be placed and implemented as computer readable code in the distributed system.

While the present invention has been particularly shown and described with reference to exemplary embodiments thereof, it will be understood by those of ordinary skill in the art that various changes in form and details may be made therein without departing from the spirit and scope of the invention as defined by the appended claims. The exemplary embodiments should be considered in descriptive sense only and not for purposes of limitation. For example, each component described as a single form may be divided and dispersed, and components described as being dispersed may be combined in a single form.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasound imaging apparatus comprising:
   a beamformer to transmit or receive an ultrasound signal;
   a first probe connection unit in which a first probe connector connected to a first probe is placed; and
   a second probe connection unit in which a second probe connector connected to a second probe is placed and configured to be connected to the first probe connection unit,
   wherein the second probe connection unit is connected to the beamformer via the first probe connection unit, and
   the first probe connection unit comprises a disconnecting unit to disconnect the first probe connection unit and the second probe connection unit from each other.

2. The ultrasound imaging apparatus according to claim 1, further comprising a controller to control the first and second probe connection units, and
   wherein the first probe connection unit comprises a locking unit to lock the first probe connector into the first probe connection unit and the second probe connection unit comprises a locking unit to lock the second probe connector into the second probe connection unit, based on a control signal generated by the controller.

3. The ultrasound imaging apparatus according to claim 2, wherein, when the first probe connector is locked into the first probe connection unit, the disconnecting unit disconnects the first probe connection unit and the second probe connection unit from each other.

4. The ultrasound imaging apparatus according to claim 1, wherein the first and second probe connectors are locked into the first and second probe connection units, respectively, through a user's manual manipulation.

5. The ultrasound imaging apparatus according to claim 1, wherein the disconnecting unit comprises at least one among an analog switch, a field-effect transistor (FET), an integrated circuit, and micro-electromechanical systems (MEMS) to disconnect the first probe connection unit and the second probe connection unit.

6. The ultrasound imaging apparatus according to claim 1, wherein the first probe connection unit further comprises a socket pin configured to transmit or receive an ultrasound signal when the socket pin comes in contact with an connection pin of the first probe connector, and
   the disconnecting unit disconnects the first probe connection unit and the second probe connection unit when the connection pin comes in contact with the socket pin.

7. The ultrasound imaging apparatus according to claim 6, wherein the socket pin is formed in a convex shape and connected to the beamformer and the disconnecting unit, and
   the disconnecting unit is connected to the socket pin, the beamformer, and the second probe connection unit, and disconnects the first probe connection unit and the second probe connection unit when a physical force is applied to a convex portion of the socket pin.

8. The ultrasound imaging apparatus according to claim 6, wherein the socket pin has a convex portion, one end of the socket pin is connected to the beamformer, and the socket pin is connected to the disconnecting unit when another end of the socket pin comes in contact with the disconnecting unit,
   one end of the disconnecting unit is connected to the second probe connection unit, and the disconnecting unit is connected to the socket pin when the socket pin comes in contact with the disconnecting unit, and
   the other end of the socket pin is separated from the other end of the disconnecting unit when a physical force is applied to the convex portion of the socket pin.

9. The ultrasound imaging apparatus according to claim 6, wherein the socket pin has a central protruding portion, a central end of the socket pin is connected to the beamformer, both ends of the socket pin are connected to the second probe connection unit, and a plurality of holes are formed in the both ends of the socket pin, through which the disconnecting unit passes, and
   one end of the disconnecting unit passes through one of the plurality of holes as the disconnecting unit is moved to the left or the right, and another end of the disconnecting unit causes the socket pin to be separated from the second probe connection unit.

10. The ultrasound imaging apparatus according to claim 9, further comprising a controller to control the disconnecting unit, and
    wherein the disconnecting unit is moved to the left or the right according to a control signal generated by the controller or through a user's manipulation.

11. The ultrasound imaging apparatus according to claim 6, wherein the first probe connection unit further comprises a driving device to cause the connection pin of the first probe connector and the socket pin to contact each other.

12. The ultrasound imaging apparatus according to claim 1, further comprising a controller to control the disconnecting unit, and
    wherein the disconnecting unit changes a direction in which the first probe connection unit and the second probe connection unit are to be disconnected from each other, according to a control signal generated by the controller or through a user's manipulation.

13. The ultrasound imaging apparatus according to claim 1, further comprising an input device to receive a command to select the first probe or the second probe from a user,
wherein, when the first probe is selected, the disconnecting unit disconnects the first probe connection unit and the second probe connection unit from each other.

14. The ultrasound imaging apparatus according to claim 1, further comprising a third probe connection unit in which a third probe connector is placed,
wherein the third probe connection unit is connected to the beamformer via the first and second probe connection units, and
the second probe connection unit comprises a disconnecting unit to disconnect the second probe connection unit and the third probe connection unit from each other.

15. The ultrasound imaging apparatus according to claim 1, further comprising a third probe connection unit in which a third probe connector is placed,
wherein the third probe connection unit is connected to the beamformer via the first and second probe connection units, and
the second probe connection unit comprises a disconnecting unit to disconnect the second probe connection unit and the third probe connection unit from each ot.

16. A method of controlling an ultrasound imaging apparatus which includes a first probe connection unit in which a first probe connector connected to a first probe is placed and a second probe connection unit in which a second probe connector connected to a second probe is placed and configured to be connected to the first probe connection unit, the method comprising:
receiving a command to select the first probe or the second probe from a user;
locking the first probe connector including the first probe when the first probe is selected; and
disconnecting the second probe connection unit, which is connected to the beamformer via the first probe connection unit, from the first probe connection unit.

17. An ultrasound imaging apparatus comprising:
a beamformer to transmit or receive an ultrasound signal;
a first probe connection unit in which a first probe connector connected to a first probe is placed;
a second probe connection unit in which a second probe connector connected to a second probe is placed and configured to be connected to the first probe connection unit, the second probe connection unit connected to the beamformer via the first probe connection unit; and
a disconnecting unit to disconnect the first probe connection unit and the second probe connection unit.

18. The ultrasound imaging apparatus according to claim 17, further comprising a controller to control the first and second probe connection units, and
wherein the first probe connection unit comprises a locking unit to lock the first probe connector into the first probe connection unit and the second probe connection unit comprises a locking unit to lock the second probe connector into the second probe connection unit, based on a control signal generated by the controller.

19. The ultrasound imaging apparatus according to claim 17, wherein the disconnecting unit comprises at least one among an analog switch, a field-effect transistor (FET), an integrated circuit, and micro-electromechanical systems (MEMS) to disconnect the first probe connection unit and the second probe connection unit.

20. The ultrasound imaging apparatus according to claim 17, wherein the disconnecting unit causes a transmission line of the first probe connection unit and a transmission line of the second probe connection unit to be separated from each other or to contact each other.

21. The ultrasound imaging apparatus according to claim 17, wherein the first and second probe connectors are locked into the first and second probe connection units, respectively, through a user's manual manipulation.

22. A method of controlling an ultrasound imaging apparatus which includes a first probe connection unit in which a first probe connector is placed and a second probe connection unit in which a second probe connector is placed, the method comprising:
receiving a command to select a first probe or a second probe from a user;
locking the first probe connector including the first probe when the first probe is selected; and
disconnecting the second probe connection unit, which is connected to the beamformer via the first probe connection unit, from the first probe connection unit,
wherein the first probe connector is connected to the first probe, and
wherein the second probe connector is connected to the second probe and is configured to be connected to the first probe connection unit.

* * * * *